(12) United States Patent
Mochitate

(10) Patent No.: US 8,304,238 B2
(45) Date of Patent: Nov. 6, 2012

(54) CELL CULTURE MEDIUM AND IMMOBILIZED PREPARATION OF CELL ADHESION PROTEIN OR PEPTIDE

(75) Inventor: Katsumi Mochitate, Tsukuba (JP)

(73) Assignees: Nat'l Institute for Environmental Studies, Tsukuba-shi, Ibaraki (JP); Katsumi Mochitate, Tsukuba-shi, Ibaraki (JP)

( * ) Notice: Subject to any disclaimer, the term of this patent is extended or adjusted under 35 U.S.C. 154(b) by 1544 days.

(21) Appl. No.: 10/551,052

(22) PCT Filed: Mar. 24, 2004

(86) PCT No.: PCT/JP2004/004077
§ 371 (c)(1),
(2), (4) Date: Jul. 13, 2006

(87) PCT Pub. No.: WO2004/085606
PCT Pub. Date: Oct. 7, 2004

(65) Prior Publication Data
US 2006/0263878 A1 Nov. 23, 2006

(30) Foreign Application Priority Data

Mar. 24, 2003 (JP) ................................. 2003-081147
Mar. 24, 2003 (JP) ................................. 2003-081148

(51) Int. Cl.
*C12N 5/00* (2006.01)
(52) U.S. Cl. ........ 435/402; 435/395; 435/396; 435/180; 530/815
(58) Field of Classification Search .................. 435/395, 435/396, 402, 180; 530/815
See application file for complete search history.

(56) References Cited

U.S. PATENT DOCUMENTS

| 4,789,601 | A  | * | 12/1988 | Banes ........................... 428/447 |
| 5,200,181 | A  | * | 4/1993 | Soltys et al. .................. 424/94.3 |
| 6,503,490 | B2 | * | 1/2003 | Johnson et al. .................. 424/65 |
| 2001/0007001 | A1 | * | 7/2001 | Rodriguez et al. ............. 525/274 |
| 2002/0182241 | A1 | * | 12/2002 | Borenstein et al. ............ 424/422 |
| 2003/0099925 | A1 | * | 5/2003 | Boone .............................. 435/4 |
| 2004/0043508 | A1 | * | 3/2004 | Frutos et al. .................. 436/518 |
| 2004/0082011 | A1 | * | 4/2004 | Matsuura et al. ............... 435/7.2 |
| 2006/0038120 | A1 | * | 2/2006 | Lean et al. ..................... 250/288 |
| 2007/0065415 | A1 | * | 3/2007 | Kleinsek et al. ............. 424/93.7 |

FOREIGN PATENT DOCUMENTS

| JP | 2-501529 | 5/1990 |
| JP | 5-176761 | 7/1993 |
| JP | 5-209072 | 8/1993 |
| JP | 5-285217 | 11/1993 |
| JP | 7-191034 | 7/1995 |
| JP | 7-222920 | 8/1995 |
| JP | 8-94621 | 4/1996 |
| JP | 10-110104 | 4/1998 |
| JP | 2002-65246 | 3/2002 |
| JP | 2002-263183 | 9/2002 |

OTHER PUBLICATIONS

Stakheeva-Kaverzneva Zhurnal Obschei Khimi (1943) 13: 408-424 (abstract). Downloaded from STN, file Caplus on Oct. 9, 2009.*
Nerurkar et al. (J. Clin. Microbiol. (1984) 29(1): 109-114.*
Satoh et al. Anal. Biochem. (1998) 260: 96-102.*
Nomizu et al. FEBS Letters (1996) 396: 37-42.*
Okazaki et al. Peptide Science (2002; volume date 2001) 38: 213-216.*
Makino et al. Peptide Science (1999) 36: 205-208.*
Kadoya et al. Developmental Biol. (2003) 263: 153-164.*
Okazaki et al. J. Biol. Chem. (2002) 277(40): 37070-37078.*
Utani et al. J. Biol. Chem. (2001) 276(31): 28779-28788.*
Kato et al. Peptide Science ((2000; volume date 2001) 37: 251-254.*
PCT International Preliminary Report on Patentability (Form PCT/IB/373) dated Feb. 22, 2006.
PCT Written Opinion of the International Searching Authority (Form PCT/ISA/237) dated Feb. 22, 2006 issued in International Application No. PCT/JP2004/004077.

* cited by examiner

*Primary Examiner* — Susan Hanley
(74) *Attorney, Agent, or Firm* — Westerman, Hattori, Daniels & Adrian, LLP

(57) ABSTRACT

The invention relates to an immobilized preparation of a cell adhesion protein or peptide for cell culture having a hydrophobic cell culture substrate, a cell adhesion protein or peptide and a hydrophobic binding-adsorptive polymer to which the cell adhesion protein or peptide has been covalently bound. The hydrophobic binding-adsorptive polymer to which the cell adhesion protein or peptide is covalently bound is adsorbed to the hydrophobic cell culture substrate by hydrophobic binding and not by chemical bonding. The hydrophobic binding-adsorptive polymer is a copolymer of maleic anhydride and styrene, a copolymer of maleic anhydride and butyl vinyl ether or a copolymer of maleic anhydride and hexyl vinyl ether.

3 Claims, 19 Drawing Sheets

SEQUENCE LISTING

```
<160> NUMBER OF SEQ ID NOS: 23

<210> SEQ ID NO 1
<211> LENGTH: 12
<212> TYPE: PRT
<213> ORGANISM: Mouse
<220> FEATURE:
<223> OTHER INFORMATION: AG73

<400> SEQUENCE: 1

Arg Lys Arg Leu Gln Val Gln Leu Ser Ile Arg Thr
1               5                   10

<210> SEQ ID NO 2
<211> LENGTH: 12
<212> TYPE: PRT
<213> ORGANISM: mouse
<220> FEATURE:
<223> OTHER INFORMATION: AG73T

<400> SEQUENCE: 2

Leu Gln Gln Arg Arg Ser Val Leu Arg Thr Lys Ile
1               5                   10

<210> SEQ ID NO 3
<211> LENGTH: 12
<212> TYPE: PRT
<213> ORGANISM: mouse
<220> FEATURE:
<223> OTHER INFORMATION: AG81.2

<400> SEQUENCE: 3

Val Lys Thr Glu Tyr Ile Lys Arg Lys Ala Phe Met
1               5                   10
```

<210> SEQ ID NO 4
<211> LENGTH: 12
<212> TYPE: PRT
<213> ORGANISM: mouse
<220> FEATURE:
<223> OTHER INFORMATION: AG81.2X
<220> FEATURE:
<221> NAME/KEY: MISC_FEATURE
<222> LOCATION: (12)..(12)
<223> OTHER INFORMATION: Nle

<400> SEQUENCE: 4

Val Lys Thr Glu Tyr Ile Lys Arg Lys Ala Phe Xaa
1               5                   10

<210> SEQ ID NO 5
<211> LENGTH: 12
<212> TYPE: PRT
<213> ORGANISM: mouse
<220> FEATURE:
<223> OTHER INFORMATION: A2G73

<400> SEQUENCE: 5

Lys Asn Arg Leu Thr Ile Glu Leu Glu Val Arg Thr
1               5                   10

<210> SEQ ID NO 6
<211> LENGTH: 12
<212> TYPE: PRT
<213> ORGANISM: mouse
<220> FEATURE:
<223> OTHER INFORMATION: A3G72

<400> SEQUENCE: 6

Lys Pro Arg Leu Gln Phe Ser Leu Asp Ile Gln Thr
1               5                   10

<210> SEQ ID NO 7
<211> LENGTH: 12
<212> TYPE: PRT
<213> ORGANISM: mouse
<220> FEATURE:
<223> OTHER INFORMATION: A4G82

<400> SEQUENCE: 7

Thr Leu Phe Leu Ala His Gly Arg Leu Val Phe Met
1               5                   10

<210> SEQ ID NO 8
<211> LENGTH: 12
<212> TYPE: PRT
<213> ORGANISM: mouse
<220> FEATURE:
<223> OTHER INFORMATION: A4G82X
<220> FEATURE:
<221> NAME/KEY: MISC_FEATURE
<222> LOCATION: (12)..(12)
<223> OTHER INFORMATION: Nle

<400> SEQUENCE: 8

Thr Leu Phe Leu Ala His Gly Arg Leu Val Phe Xaa
1               5                   10

<210> SEQ ID NO 9
<211> LENGTH: 12
<212> TYPE: PRT
<213> ORGANISM: mouse
<220> FEATURE:

<223> OTHER INFORMATION: A5G71

<400> SEQUENCE: 9

Gly Pro Leu Pro Ser Tyr Leu Gln Phe Val Gly Ile
1               5                   10

<210> SEQ ID NO 10
<211> LENGTH: 12
<212> TYPE: PRT
<213> ORGANISM: mouse
<220> FEATURE:
<223> OTHER INFORMATION: A5G73

<400> SEQUENCE: 10

Arg Asn Arg Leu His Leu Ser Met Leu Val Arg Pro
1               5                   10

<210> SEQ ID NO 11
<211> LENGTH: 12
<212> TYPE: PRT
<213> ORGANISM: mouse
<220> FEATURE:
<223> OTHER INFORMATION: A5G73X
<220> FEATURE:
<221> NAME/KEY: MISC_FEATURE
<222> LOCATION: (8)..(8)
<223> OTHER INFORMATION: Nle

<400> SEQUENCE: 11

Arg Asn Arg Leu His Leu Ser Xaa Leu Val Arg Pro
1               5                   10

<210> SEQ ID NO 12
<211> LENGTH: 12
<212> TYPE: PRT
<213> ORGANISM: mouse
<220> FEATURE:
<223> OTHER INFORMATION: A5G77

<400> SEQUENCE: 12

Leu Val Leu Phe Leu Asn His Gly His Phe Val Ala
1               5                   10

<210> SEQ ID NO 13
<211> LENGTH: 9
<212> TYPE: PRT
<213> ORGANISM: mouse
<220> FEATURE:
<223> OTHER INFORMATION: A5G77f

<400> SEQUENCE: 13

Leu Val Leu Phe Leu Asn His Gly His
1               5

<210> SEQ ID NO 14
<211> LENGTH: 12
<212> TYPE: PRT
<213> ORGANISM: Homo sapiens

<400> SEQUENCE: 14

Lys Asn Ser Phe Met Ala Leu Thr Tyr Ser Lys Gly
1               5                   10

<210> SEQ ID NO 15
<211> LENGTH: 12
<212> TYPE: PRT
<213> ORGANISM: Homo sapiens
<220> FEATURE:

<223> OTHER INFORMATION: hA3g83

<400> SEQUENCE: 15

Gly Asn Ser Thr Ile Ser Ile Arg Ala Pro Val Tyr
1               5                   10

<210> SEQ ID NO 16
<211> LENGTH: 12
<212> TYPE: PRT
<213> ORGANISM: Homo sapiens
<220> FEATURE:
<223> OTHER INFORMATION: FIB-1

<400> SEQUENCE: 16

Tyr Ala Val Thr Gly Arg Gly Asp Ser Pro Ala Ser
1               5                   10

<210> SEQ ID NO 17
<211> LENGTH: 12
<212> TYPE: PRT
<213> ORGANISM: mouse
<220> FEATURE:
<223> OTHER INFORMATION: AG76.8

<400> SEQUENCE: 17

Thr Leu Gln Leu Gln Glu Gly Arg Leu His Phe Met
1               5                   10

<210> SEQ ID NO 18
<211> LENGTH: 12
<212> TYPE: PRT
<213> ORGANISM: mouse
<220> FEATURE:
<223> OTHER INFORMATION: AG76.8X
<220> FEATURE:
<221> NAME/KEY: MISC_FEATURE
<222> LOCATION: (12)..(12)
<223> OTHER INFORMATION: Nle

<400> SEQUENCE: 18

Thr Leu Gln Leu Gln Glu Gly Arg Leu His Phe Xaa
1               5                   10

<210> SEQ ID NO 19
<211> LENGTH: 12
<212> TYPE: PRT
<213> ORGANISM: mouse
<220> FEATURE:
<223> OTHER INFORMATION: A4G73

<400> SEQUENCE: 19

Lys Phe Leu Glu Gln Lys Ala Pro Arg Asp Ser His
1               5                   10

<210> SEQ ID NO 20
<211> LENGTH: 12
<212> TYPE: PRT
<213> ORGANISM: mouse
<220> FEATURE:
<223> OTHER INFORMATION: A4G78

<400> SEQUENCE: 20

Gly Glu Lys Ser Gln Phe Ser Ile Arg Leu Lys Thr
1               5                   10

<210> SEQ ID NO 21
<211> LENGTH: 12
<212> TYPE: PRT

```
<213> ORGANISM: human
<220> FEATURE:
<223> OTHER INFORMATION: hA3G75

<400> SEQUENCE: 21

Lys Asn Ser Phe Met Ala Leu Tyr Leu Ser Lys Gly
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Chemically Synthesized

<400> SEQUENCE: 22

Gly Arg Gly Asp Ser Pro
1               5

<210> SEQ ID NO 23
<211> LENGTH: 5
<212> TYPE: PRT
<213> ORGANISM: Artificial Sequence
<220> FEATURE:
<223> OTHER INFORMATION: Chemically Synthesized

<400> SEQUENCE: 23

Tyr Ala Val Thr Gly
1               5
```

CELL CULTURE MEDIUM AND IMMOBILIZED PREPARATION OF CELL ADHESION PROTEIN OR PEPTIDE

TECHNICAL FIELD

The present invention relates to a cell culture substrate whose surface is coated with a hydrophobic binding-adsorptive polymer, an immobilized preparation of cell adhesion proteins or peptides bound to the cell culture substrate, and further, an artificial tissue prepared by seeding and culturing cells on the immobilized preparation.

BACKGROUND ART

An epithelial tissue, which is a cell layer covering the inside and outside surface of an animal body, such as an epidermis, a corneal epithelium, an alveolar epithelium, a mucosal epithelium of digestive system, renal glomerular epithelium, and hepatic parenchymal cells, prevents the invasion of an exogenous material (microorganism, allergen, chemical substance, etc.) from the external world. The outer interface of epithelial cells that constitutes said epithelial tissue is called apical surface, and the inside undersurface is called basal surface. Just beneath said basal surface, there is a thin film structure of 50-100 nm thickness called a basement membrane comprised of extracellular matrices (ECM) such as proteins, and proteoglycans, which does not include cells. A basement membrane is considered to be an essential structure for immature epithelial cells to proliferate, to differentiate into mature cells, and to express its intrinsic morphology and function. In other words, without a basement membrane, an epithelial tissue cannot maintain itself or achieve its intrinsic performance. Although an epithelial cell layer of multi-layer or monolayer prevents the invasion of an exogenous material from the external world as a barrier, a basement membrane itself also acts as a physical barrier. Thus, epithelial cells constituting an epithelial tissue collaborate with a basement membrane to form a solid barrier and to protect the internal vital activity.

A basement membrane, which is a specific membranous structure of extracellular matrices formed on the interface between parenchymal cells, such as epithelial cells, endothelial cells, muscle cells, adipocytes, Schwann cells, and connective tissues, is universally found in respective tissue/organ of a living body, however, some kinds of basement membranes are highly specialized such as a renal glomerular capillary loop, a nervous synapse membrane. Thus, it is disclosed that the basement membrane has not only a function to allow cells to adhere to interstitium, but also a function of selective permeability about substance/cell, and to induce the differentiation of cells. In renal glomerulus, negative electric charges of a basement membrane are considered to be responsible for the filtration function of kidney, and said negative electric charges are traditionally known to be due to heparan sulfate proteoglycan (HSPG) which is currently called perlecan. HSPG is widely distributed not only to the renal glomerular basement membrane but also to various kinds of basement membranes as a basic component of basement membrane, just like type IV collagen, laminin, entactin (nidogen), etc.

An extracellular matrix, especially a basement membrane, is now gradually known to be deeply involved not only in the physiological phenomena such as generation and differentiation of an individual as described above, but also in the formation of pathology such as proliferative metastasis of cancer and inflammation. Therefore, clarification of the function of its constituent protein has been an important task. For example, laminin, which is a main glycoprotein of basement membrane, is a complex comprised of three subunits α, β, and γ, fifteen types of its isoforms are known, and they are expressed tissue-specifically, or specifically at each step of development. Laminin is a complicated macromolecule of 900,000 molecular weight having various bioactivities. As laminin receptors, integrin molecule such as α6β1, α-dystroglycan (α-DG), heparan sulfate proteoglycan (HSPG) of syndecan-1 to -4 are reported.

The interaction between a component of basement membrane, which is a thin extracellular matrix layer to which cells can adhere, and epithelial cells influences the cell function such as migration, proliferation, and differentiation (Crouch et al., Basement membrane. In The Lung (ed. R. G. Crystal and J. B. West), pp 53.1-53.23. Philadelphia: Lippincott-Raven. 1996). As for the main components of basement membrane, laminin, type IV collagen, heparan sulfate proteoglycan (HSPG), and entactin (nidogen) are known as described above (Curr. Opin. Cell Biol. 6, 674-681, 1994), and mesenchymal cells are considered to play an important role for the synthesis of basement membrane components including isoforms of laminin and type IV collagen (Matrix Biol. 14, 209-211, 1994; J. Biol. Chem. 268, 26033-26036, 1993), however, the role of epithelial cells is also important. HSPG has been believed to be derived from epithelial cells, however, laminin, type IV collagen, and entactin (nidogen) are synthesized in vivo by both of epithelial cells and mesenchymal cells (Development, 120, 2003-2014, 1994; Gastroenterology 102, 1835-1845, 1992). Many attempts have been made to construct an epithelial tissue model in vitro showing a continuous lamina densa. Tissue models of intestine (J. Cell Biol. 133, 417-430, 1996) and skin (J. Invest. Dermatol., 105, 597-601, 1995; J. Invest. Dermatol., 109, 527-533, 1997; Dev. Dynam., 197,255-267, 1993) and the like have been studied, and some of basement membrane components derived from mesenchymal cells have been found to play an important role in the formation of basement membrane.

Several methods to constitute a basement membrane by culturing epithelial cells, and to constitute epithelial tissues wherein a basement membrane structure is present just beneath the basal surface have been reported. For example, the present inventor has reported that a basement membrane can be formed in vitro by coculturing alveolar epithelial cells and pulmonary fibroblasts (Cell Struc. Func., 22:603-614, 1997). It has been reported that when pulmonary fibroblasts are embedded in type I collagen gel and cultured, the collagen gel is contracted and becomes more solid by pulmonary fibroblasts. Extracellular matrices secreted from pulmonary fibroblasts attach to collagen fibrils around the cells and are deposited; the resultant formation is called a pseudointerstitium since it is similar to an interstitium in vivo. Basement membrane components such as laminin, type IV collagen, perlecan, entactin (nidogen) are also secreted from pulmonary fibroblasts to the culture medium. When alveolar type II epithelial cell line (SV40-T2) was cultured on such pseudo-interstitial type I collagen fibrils for approximately 14 days (T2-Fgel), basement membrane components secreted from pulmonary fibroblasts diffuse and reach the basal surface of the alveolar type II epithelial cell line described above, and are used as materials for the constitution of basement membrane, and as a result, a basement membrane structure is formed.

It is also reported that a basement membrane is formed just like the case of coculture of the above alveolar epithelial cells and pulmonary fibroblasts by the following process: the diluted neutral collagen solution was incubated at 37° C. in 5% $CO_2$, and collagen fibrils were formed, then the air-dried fibrillar collagen matrix (fib) that was air-dried in aseptic condition was used as an alternative to the pseudointerstitium described above (Eur. J. Cell Biol., 78:867-875, 1999; J. Cell Sci., 113:859-868, 2000). In this process, if the concentration of the collagen solution is high, there will be less or no space formed among fibrillar collagen, and if epithelial cells are cultured for a long term (10 days-2 weeks) for the purpose of basement membrane formation, the cells are exfoliated and floated (e.g. Becton Dickinson, Fibrillar collagen coat culture insert), therefore, the concentration of the collagen solution is considered to be optimum at 0.3-0.5 mg/ml (Eur. J. Cell. Biol., 78:867-875, 1999; J. Cell Sci., 113:859-868, 2000).

Alveolar type II epithelial cell line (SV40-T2) was cultured on a fibrillar collagen matrix coexistent with Matrigel (the registered trademark of Becton Dickinson), instead of using a collagen matrix wherein fibroblasts were embedded. In this case, Matrigel functioned as an exogenous resource of basement membrane components. Matrigel is a basement membrane preparation extracted from Engelbreth-Holm-Swarm tumor matrix (J. Exp. Med. 145, 204-220, 1977), and contains laminin-1, entactin (nidogen), type IV collagen, and perlecan, as well as various kinds of cytokines that possibly influence the synthesis of ECM (Exp. Cell Res. 202, 1-8, 1992). In order to trace the incorporation of Matrigel-derived components into a basement membrane, Matrigel was labeled with biotin. Among the labeled basement membrane components, laminin-1 and entactin (nidogen) mostly diffused into the culture medium, and were incorporated in the basement membrane formed by pulmonary epithelial cells. In addition, when basement membrane components were stained immunofluorescently and observed with a (fluorescent) microscope, the acceleration of basement membrane formation depending on the amount of Matrigel, and the process wherein basement membrane matrix components are secreted, deposited in a punctiform manner, expanded in a sheet form, and then developed into a basement membrane were observed. Based on these results, it has been found that exogenous laminin-1 and entactin (nidogen) provided from a lower part below the basal surface of alveolar epithelial cells are largely involved in the in vitro formation of a complete basement membrane by the epithelial cells described above (J. Cell Sci., 113:859-868, 2000).

Further, as a method for culturing cells comprising the attachment of cells in vitro, a method wherein an end-group activated polymer (EGAP) conjugated with a biomolecule via disulfide bond is adsorbed to the surface of hydrophobic tissue culture, and cells are seeded on the surface of the biomolecule-conjugated EGAP coating and proliferated is disclosed (Published Japanese Translation of PCT International Publication No. 2001-512565; WO98/31734).

When cultured cells adhere to a substrate, receptor molecules, such as integrin, present on the cell surface are generally used for the adhesion. Therefore, in order to induce the cell adhesion to a substrate by using specific receptors, extracellular matrices, etc. that have cell adhesion activities are used as a linker. As for representative extracellular matrices, cell adhesion proteins such as fibronectin (FN), collagen (Col), laminin (LN) and vitronectin (VN) are known. These cell adhesion proteins are used as a substrate for cell culture. In the culturing process, these cell adhesion proteins are directly adsorbed by noncovalent binding by making use of hydrophobic binding to plastic wells, and epithelial cells, vascular endothelial cells, fibroblasts, etc., are seeded thereon. However, these cell adhesion proteins are expensive and, what is more, they are susceptible to denaturation and degradation, which are general properties of proteins, and have problems with its price, stability, shelf life, etc.

In addition, a peptide in the region relating to the cell adhesion in the amino acid sequence of a cell adhesion protein can be directly adsorbed to plastic wells in the manner similar to that described above and used as a substrate for cell culture. In comparison with a method using these cell adhesion proteins, a method using peptides which can be easily chemosynthesized as cell adhesion peptides has advantages when it is used for a cell culture substrate because such peptides are easily mass-produced and these structure are relatively stable. However, because such peptides have a low molecular weight, their adsorptive efficiency is extremely lower than that of proteins, and only a few percent of them are adsorbed. Further, it is difficult for the peptides as well to bind to receptors on the cell side when they are adsorbed to plastics and deprived of the freedom of movement. In addition, even if peptides once adsorbed to the plastics the peptides will be gradually detached from there subsequently. Therefore, the reproducibility of cell adhesion using peptides is not excellent, and it (the wells where peptides are directly coated) is not highly valuable as industrial goods.

The present inventor has found a method for coating the hydrophobic surface of a well with a cell adhesion ligand (a molecule of an extracellular matrix to which a receptor binds) to induce the adhesion of cultured cells to a substrate, instead of a hydrophilically treated plastic well used for cell culture, and completed the present invention. This method makes use of noncovalent bonding (hydrophobic binding) between a ligand, a receiver of cell adhesion, and a well on which the ligand is immobilized.

In other words, the present invention is to provide: a cell culture substrate which adsorbs to cell culture substrates such as wells, and is excellent in the reproducibility of cell adhesion, and whose surface is coated with a hydrophobic binding-adsorptive polymer; the immobilized preparation of cell adhesion proteins or peptides which binds to cell culture substrates efficiently, and is excellent in the reproducibility of cell adhesion; and further, an artificial tissue prepared by seeding cells onto the immobilized preparation of cell adhesion peptides and culturing the cells.

DISCLOSURE OF THE INVENTION

The present invention relates to: a cell culture substrate coated with a hydrophobic binding-absorptive polymer having a hydrophobic linear skeleton and a functional group which can react to a protein or a peptide in a molecule, the cell culture substrate, wherein a base material of the cell culture substrate comprises a biobased polymer, plastic, natural or synthetic rubber, an inorganic material or metal, the cell culture substrate, wherein the biobased polymer is collagen, gelatin, cellulose, agarose, alginic acid, chitin, chitosan, or a biodegradable polymer, which is, polylactic acid, polybutylente succinate, or polycaprolactone, the cell culture substrate, wherein the plastic is a thermoplastic resin or a thermosetting resin, the cell culture substrate, wherein the thermoplastic resin is an acryl resin, a polyvinyl chloride resin, a polyethylene resin, a polystyrene resin, a polypropylene resin, a polymethylpentene resin or a fluorocarbon resin, the cell culture substrate, wherein the thermosetting resin is a phenolic resin, an urea formaldehyde resin, an epoxy resin, a melamine resin or a silicone resin, the cell culture substrate, wherein the synthetic rubber is butadiene-styrene rubber, butadiene-acrylonitrile rubber, butyl rubber, polysulfide-based synthetic rubber, fluorocarbon rubber or silicone rubber, the cell culture substrate, wherein the inorganic material is glass, hydroxyapatite, IC substrate or a carbon nanotube, the cell culture substrate, wherein the metal is inert gold, platinum, titanium, indium, or an oxide thereof which is titanium oxide, indium oxide, or ITO (indium tin oxide), the cell culture substrate, wherein the cell culture substrate comprising a base material is a well, a printed-wiring board, or an artificial organ, the cell culture substrate, wherein the artificial organ is an artificial blood vessel, an artificial heart lung, or an artificial kidney, the cell culture substrate, wherein the cell culture substrate is a well comprising silicone as a base material, the cell culture substrate, wherein the hydrophobic binding-adsorptive polymer is shown by the following formula [I]:

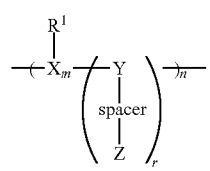

(wherein, X denotes CH or NHCHCO, Y denotes CH or NHCR²CO, R¹ denotes H, alkyl group of carbon number 1 to 10, alkoxy group of carbon number 1 to 10, aryl or aralkyl group of carbon number 6 to 10, or aryloxy or aralkyloxy group of carbon number 6 to 10, R² denotes H or alkyl group of carbon number 1 to 10, Z denotes a functional group (reactive group) and is optionally bonded to X reciprocally, spacer denotes (—CH$_2$—)$_p$ or (—NHCHR³CO—)$_q$, R³ denotes H or alkyl group of carbon number 1 to 10, m denotes an integral number greater or equal to 1, n denotes an integral number between 100 and 20000, p and q independently denote 0 or integral numbers 1 to 8, and r denotes an integral number greater or equal to 1), the cell culture substrate, wherein the hydrophobic binding-adsorptive polymer shown by the formula [I] is a copolymer made of a vinyl-based compound and maleic anhydride, and the cell culture substrate, wherein the vinyl-based compound is methyl vinyl ether, ethyl vinyl ether, butyl ether, hexyl vinyl ether or styrene.

The present invention also relates to: an immobilized preparation of a cell adhesion protein or peptide wherein the cell adhesion protein or peptide is bound to the cell culture substrate, the immobilized preparation, wherein the binding is covalent bonding formed by a reaction between a functional group, which is capable of reacting to a protein or a peptide, of a hydrophobic binding-adsorptive polymer and a reactive group of a cell adhesion protein or peptide, the immobilized preparation, wherein the covalent bonding is amide bonding, the immobilized preparation, wherein the cell adhesion protein is fibronectin (FN), collagen (Col), laminin (LN) or vitronectin (VN), the immobilized preparation, wherein the cell adhesion peptide is a peptide in a region relating to cell adhesion in an amino acid sequence of the cell adhesion protein, the immobilized preparation, wherein the peptide in a region relating to cell adhesion of fibronectin (FN) protein is a peptide having a specific Arg-Gly-Asp (RGD) amino acid sequence which binds to an integrin receptor on a cell side, the immobilized preparation, wherein the peptide having an RGD amino acid sequence is Tyr-Ala-Val-Thr-Gly-Arg-Gly-Asp-Ser-Pro-Ala-Ser (FIB-1) (SEQ ID NO: 16), the immobilized preparation, wherein the peptide in a region relating to cell adhesion of laminin (LN) protein is an α-chain G-domain peptide, the immobilized preparation, wherein the G-domain peptide is Arg-Lys-Arg-Leu-Gln-Val-Gln-Leu-Ser-Ile-Arg-Thr (AG73) (SEQ ID NO: 1), Leu-Gln-Gln-Arg-Arg-Ser-Val-Leu-Arg-Thr-Lys-Ile (AG73T) (SEQ ID NO: 2), Thr-Leu-Gln-Leu-Gln-Glu-Gly-Arg-Leu-His-Phe-Met (AG76.8) (SEQ ID NO: 17), Thr-Leu-Gln-Leu-Gln-Glu-Gly-Arg-Leu-His-Phe-Nle (AG76.8X) (SEQ ID NO: 18), Val-Lys-Thr-Glu-Tyr-Ile-Lys-Arg-Lys-Ala-Phe-Met (AG81.2) (SEQ ID NO: 3), Val-Lys-Thr-Glu-Tyr-Ile-Lys-Arg-Lys-Ala-Phe-Nle (AG81.2X) (SEQ ID NO: 4), Lys-Asn-Arg-Leu-Thr-Ile-Glu-Leu-Glu-Val-Arg-Thr (A2G73) (SEQ ID NO: 5), Lys-Pro-Arg-Leu-Gln-Phe-Ser-Leu-Asp-Ile-Gln-Thr (A3G72) (SEQ ID NO: 6), Lys-Phe-Leu-Glu-Gln-Lys-Ala-Pro-Arg-Asp-Ser-His (A4G73) (SEQ ID NO: 19), Gly-Glu-Lys-Ser-Gln-Phe-Ser-Ile-Arg-Leu-Lys-Thr (A4G78) (SEQ ID NO: 20), Thr-Leu-Phe-Leu-Ala-His-Gly-Arg-Leu-Val-Phe-Met (A4G82) (SEQ ID NO: 7), Thr-Leu-Phe-Leu-Ala-His-Gly-Arg-Leu-Val-Phe-Nle (A4G82X) (SEQ ID NO: 8, Gly-Pro-Leu-Pro-Ser-Tyr-Leu-Gln-Phe-Val-Gly-Ile (A5G71) (SEQ ID NO: 9), Arg-Asn-Arg-Leu-His-Leu-Ser-Met-Leu-Val-Arg-Pro (A5G73) (SEQ ID NO: 10), Arg-Asn-Arg-Leu-His-Leu-Ser-Nle-Leu-Val-Arg-Pro (A5G73X) (SEQ ID NO: 11), Leu-Val-Leu-Phe-Leu-Asn-His-Gly-His-Phe-Val-Ala (A5G77) (SEQ ID NO: 12), Leu-Val-Leu-Phe-Leu-Asn-His-Gly-His (A5G77f) (SEQ ID NO: 13), Lys-Asn-Ser-Phe-Met-Ala-Leu-Tyr-Leu-Ser-Lys-Gly (hA3G75) (SEQ ID NO: 21) or Gly-Asn-Ser-Thr-Ile-Ser-Ile-Arg-Ala-Pro-Val-Tyr (hA3G83) (SEQ ID NO: 15), the immobilized preparation, wherein the cell adhesion peptide is a peptide comprising 3 to 20 amino acid residues, a method for producing a immobilized preparation wherein a functional group, which is capable of reacting to a protein or a peptide, of a hydrophobic binding-adsorptive polymer coated on a cell culture substrate reacts to a cell adhesion protein or peptide, a method for producing a immobilized preparation wherein a functional group, which is capable of reacting to a protein or a peptide, of a hydrophobic binding-adsorptive polymer reacts to a cell adhesion protein or peptide, and a cell culture substrate is coated with the reactant, and a reactant obtained by reacting a functional group, which is capable of reacting to a protein or a peptide, of a hydrophobic binding-adsorptive polymer, to a cell adhesion protein or peptide.

The present invention further relates to: an artificial tissue prepared by seeding a desired cell on the immobilized preparation of a cell adhesion protein or peptide, and culturing the cell, the artificial tissue, wherein the desired cell is an epithelial cell, an endothelial cell or a mesenchymal cell, the artificial tissue, wherein the epithelial cell is an epidermal cell, a corneal epithelial cell, an alveolar epithelial cell, a mucosal epithelial cell of digestive system, a renal glomerular epithelial cell or a hepatic parenchymal cell, the artificial tissue, wherein the endothelial cell is a renal glomerular ciliated cell, a vascular endothelial cell, a pulmonary arterial vascular endothelial cell, a placental venous vascular endothelial cell or an aortic endothelial cell, the artificial tissue, wherein the mesenchymal cell is a muscle cell, an adipocyte, a glial cell, a Schwann cell or a neural cell (neuron) the artificial tissue, wherein the artificial tissue is an artificial epidermal tissue, an artificial corneal epithelial tissue, an artificial alveolar epithelial tissue, an artificial respiratory epithelial tissue, an artificial renal glomerular tissue, an artificial hepatic parenchymal tissue or an artificial vascular endothelial tissue, or an artificial blood vessel, an artificial lung, an artificial liver, an artificial kidney, an artificial skin or an artificial cornea.

BEST MODE OF CARRYING OUT THE INVENTION

Figure 1:
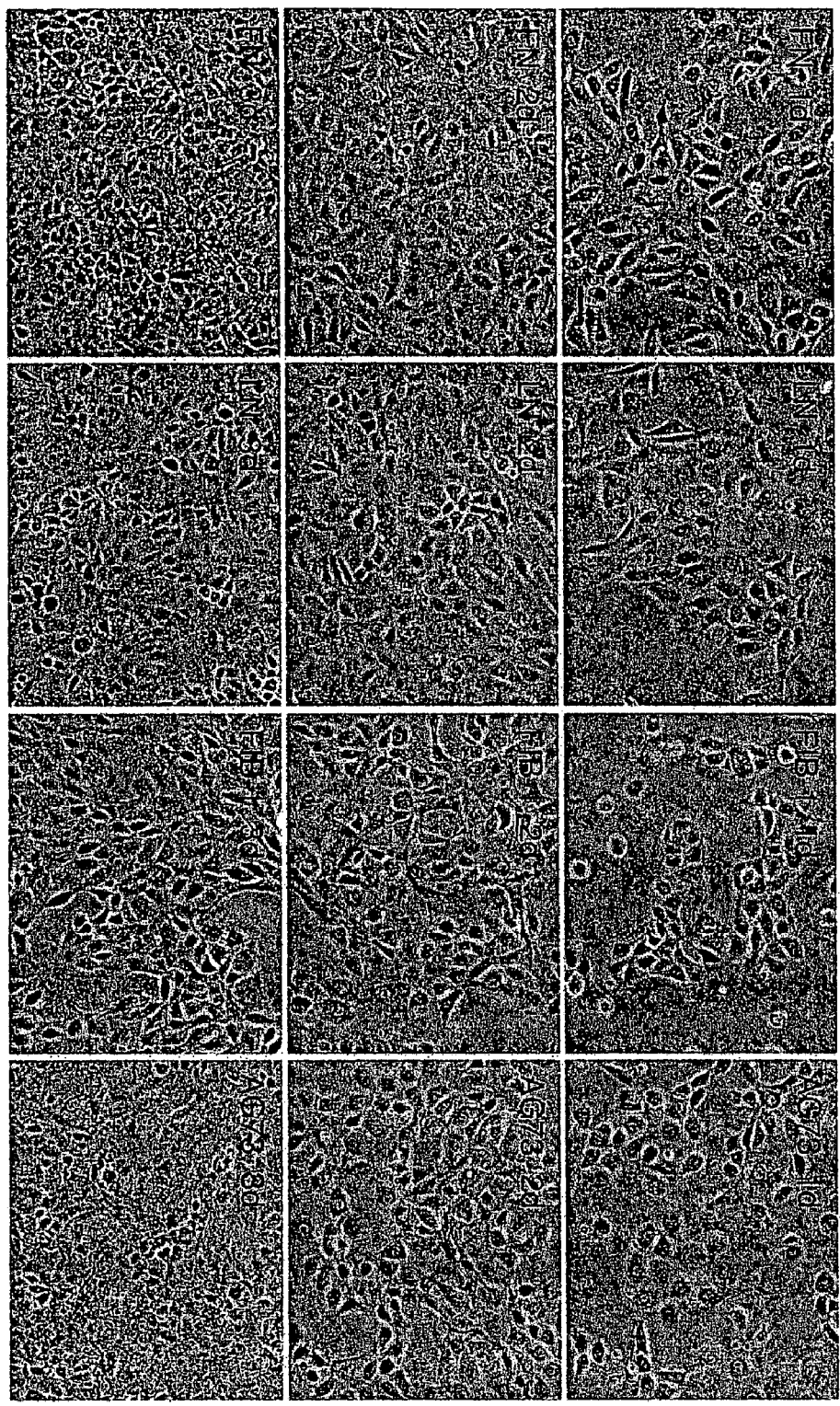
FIG. 1 is a set of phase contrast micrographs of alveolar epithelial tissues formed as a result of static culture of alveolar type II epithelial cells (T2 cells) on a silicone well wherein extracellular matrix proteins and cell adhesion peptides were immobilized by using MMAC of a hydrophobic binding-adsorptive polymer.

The cell culture substrate of the present invention is exemplified by those using, for example, biobased polymers, plastics, natural or synthetic rubbers, inorganic materials or metals, etc., as a base material.

Examples of the biobased polymers include collagen, gelatin, cellulose, agarose, alginic acid, chitin, chitosan, or polylactic acid, polybutylente succinate, and polycaprolactone, which are biodegradable polymers.

Either of thermoplastic resins or thermosetting resins can be used as the plastics, and examples of the thermoplastic resins include acryl resins, polyvinyl chloride resins, polyethylene resins, polystyrene resins, polypropylene resins, polymethylpentene resins and fluorocarbon resins, and examples of the thermosetting resins include phenolic resins, urea formaldehyde resins, epoxy resins, melamine resins and silicone resins.

As the synthetic rubbers, butadiene-styrene rubbers, butadiene-acrylonitrile rubbers, butyl rubbers, polysulfide-based synthetic rubbers, fluorocarbon rubbers and silicone rubbers, etc., are exemplified, and silicone rubbers are particularly preferable among them.

Examples of the inorganic materials include glass, hydroxyapatite, IC substrates such as silicon, and carbon nanotubes.

As the metals, inert gold, platinum, titanium, indium, or oxides thereof, for instance, titanium oxide, indium oxide, ITO (indium tin oxide), etc., are exemplified.

With regard to glass, in particular, glass had been used as a cell culture substrate before plastic became generalized as today. However, glass has been replaced by plastic nowadays because of its instability of adhesion efficiency, the asperity of its surface due to repeated use, etc. Its optical transparency is, however, an excellent property, and the present invention can be applied to glass with flat surface or surface-treated glass, as well.

Cell culture substrate are used for wells, printed-wiring boards, or artificial organs, etc., and examples of the artificial organs include artificial blood vessels, artificial heart lungs, and artificial kidneys. In addition, wells made with silicone rubber as a base material are preferably used.

With regard to the hydrophobic binding-adsorptive polymer, it has a hydrophobic linear skeleton and a functional group that can react to a protein or a peptide in a molecule, and is shown by the following formula [I]:

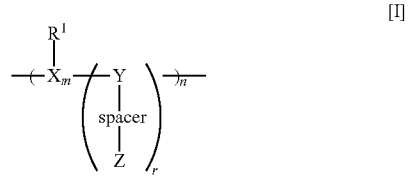

(wherein, X denotes CH or NHCHCO, Y denotes CH or NHCR$^2$CO, R$^1$ denotes H, alkyl group of carbon number 1 to 10, alkoxy group of carbon number 1 to 10, aryl or aralkyl group of carbon number 6 to 10, or aryloxy or aralkyloxy group of carbon number 6 to 10, R$^2$ denotes H or alkyl group of carbon number 1 to 10, Z denotes a functional group (reactive group), and is optionally bonded to X reciprocally, spacer denotes (—CH$_2$—)p or (—NHCHR$^3$CO—)q, R$^3$ denotes H or alkyl group of carbon number 1 to 10, m denotes an integral number greater or equal to 1, n denotes an integral number between 100 and 20000, p and q independently denote 0 or integral numbers 1 to 8, and r denotes an integral number greater or equal to 1).

In the formula [I], examples of the alkyl group of carbon number 1 to 10 include linear or branched methyl, ethyl, propyl, butyl, pentyl, hexyl, heptyl, octyl, nonyl, and decyl groups, examples of the alkoxy group of carbon number 1 to 10 include linear or branched methoxy, ethoxy, propoxy, butoxy, pentyloxy, hexyloxy, heptyloxy, octyloxy, nonyloxy, and decyloxy groups, examples of the aryl or aralkyl group of carbon number 6 to 10 include phenyl, naphthyl, benzyl, and phenethyl groups, and examples of the aryloxy or aralkyloxy group of carbon number 6 to 10 include phenoxy, naphthoxy, benzyloxy, and phenethyloxy groups.

The functional group (reactive group) is not particularly limited as long as it can react to a reactive group of a protein or a peptide and bind thereto. Examples of the group include carboxyl, amino, mercapto, and hydroxyl groups, and reactive derivatives thereof. As reactive derivatives of carboxyl groups, reactive derivatives such as acid halide, acid anhydride, acid imide, activated ester are exemplified, and as reactive derivatives of amino groups, isocyanate groups, etc., are exemplified. In addition, acid anhydride, acid imide, etc., may bind to X and form a ring.

As for the hydrophobic binding-adsorptive polymer, a hydrophobic binding-adsorptive polymer which can adsorb to the surface of a cell culture substrate, which has a hydrophobic linear skeleton such as polyalkylene chain or linear amino acid polymer (polyglycine, polyalanine, polyvaline, polyleucine, polyphenylalanine, etc.), and its derivatives in a molecule, and which has a reactive functional group which can directly react with the hydrophobic linear skeleton or react with proteins or peptides through a spacer can be preferably used. The range of n in the formula [I] is 100-20000, the molecular weight of adsorptive polymer by hydrophobic binding shown by the formula [I] is preferable to be around 15,000-3,200,000.

Further, the hydrophobic binding-adsorptive polymer having the functional group can be exemplified by a copolymer made of one or more types selected from alkylene such as ethylene and propylene; unsaturated ether such as methyl vinyl ether, ethyl vinyl ether, ethyl-1-propenyl ether, butyl vinyl ether, hexyl vinyl ether; vinyl-based compound such as styrene; or α-amino acid such as alanine, glycine, valine, leucine, isoleucine, phenylalanine: and one or more types selected from monomers having reactive groups such as carboxylic anhydride and acid imide such as maleic anhydride, maleic imide; olefin such as acrylic acid, acrylamide, and acrylonitrile; amino acid having a mercapto group such as cysteine; amino acid having a hydroxyl group such as serine and threonine; monoamino dicarboxylic acid such as aspartic acid and glutamic acid; diamino monocarboxylic acid such as lysine. These copolymers can be copolymers wherein dimer, trimer, etc., are bilaterally copolymerized, however, it is preferable to be an alternating copolymer. Further, in the case of monomers having reactive groups, condensation homopolymerization of themselves have the structure with functional group, without involving a spacer, in hydrophobic linear skeleton formed by condensation, therefore, they can be adopted as a hydrophobic binding-adsorptive polymer having a functional group of the present invention.

Among them, a copolymer of maleic anhydride and vinyl-based compound such as methyl vinyl ether, ethyl vinyl ether, ethyl-1-propenyl ether, butyl vinyl ether, hexyl vinyl ether and styrene is representatively exemplified as the hydrophobic binding-adsorptive polymer having a functional group of the present invention. Particularly, MMAC (methyl vinyl ether/maleic anhydride copolymer) which is a copolymer of maleic anhydride and methyl vinyl ether, MBAC (butyl vinyl ether/maleic anhydride copolymer) which is a copolymer of maleic anhydride and butyl vinyl ether, MHAC (hexyl vinyl ether/maleic anhydride copolymer) which is a copolymer of maleic anhydride and hexyl vinyl ether, and MAST (styrene/maleic anhydride copolymer) which is a copolymer of maleic anhydride and styrene, are specifically exemplified. The polymers can be synthesized according to ordinary copolymerization methods of olefins, or are available as commercial products.

In the case of MMAC, MBAC, MHAC, etc., linear polymer with methylene group as a skeleton makes it possible to adsorb to the surface of cell culture substrates by hydrophobic binding, however, if it is only with polyalkylene skeleton, it is too hydrophobic and its affinity to water will lower, and there will possibly be a disadvantage for the reactivity as a result of microscopically repelling water. Therefore, regarding the one wherein some hydrogen atoms of a methylene group are substituted with, for example, an alkoxy group such as methoxy, butoxy and hexyloxy, as described above, the reaction efficiency is considered to be enhanced due to the presence of oxygen atoms. Besides, it is not preferable to substitute with hydroxyl group instead of alkoxy group since the ester bond with carboxylic acid anhydride is formed intermolecularly. Further, maleic anhydride which is a reactive group of MMAC, MBAC, MHAC, etc., is to react with and bind to amino groups or hydroxyl groups, etc. of a protein or a peptide, and it can bind to positive electric charge of the protein or the peptide by ionic bond even if this maleic anhydride becomes carboxylic acid as a result of reacting with water.

A hydrophobic binding-adsorptive polymers are appropriately selected according to the material of cell culture substrates for use and to the purposes of use. For example, the aforementioned MMAC, MBAC, MHAC, etc., are polymers having methylene skeleton, and these polymers having polyalkylene such as polyethylene and polypropylene as a main chain are flexible, therefore, they are suitable material, for example, for coating a silicone rubber well which repeats stretching movement. On the other hand, MAST, which has styrene skeleton, contains a phenyl group in its side chain and therefore, it has an excellent electrical property and an adamant skeleton structure. Due to these characteristics, it is suitably used for coating in case where base materials with high hydrophobicity and rigidity such as polystyrene, carbon nanotubes having an excellent electrical property, or metals such as gold and platinum or metal oxides (e.g., ITO) having an excellent electrical conductivity property, are used as cell culture substrates.

Besides, the above hydrophobic binding-adsorptive polymers can adsorb to the surface of cell culture substrates irrespective of types or material of the cell culture substrates, since they adsorb to the surface of the cell culture substrates by hydrophobic binding not by chemical bond due to their hydrophobic linear skeleton. The reason is as follows: even if some parts of a long main chain detached from the adhesion surface, the detached parts cannot be very far away from the adhesion surface because most of other parts are adhering. As a result, it is considered that the polymer will bind again before long to the surface of the substrate by hydrophobic bond, and that the detachment will be temporary. This hydrophobic binding-adsorptive polymer can strongly bind to cell culture substrates with its long hydrophobic main chain, even if the substrate comprises a material to which cell adhesion proteins or peptides cannot achieve strong hydrophobic bonding.

A method for coating cell culture substrates with a hydrophobic binding-adsorptive polymer comprises applying a solution of hydrophobic binding-adsorptive polymer, which has been prepared in advance by dissolving in a solvent, to cell culture substrates, and then drying it. When a solution of hydrophobic binding-adsorptive polymer is applied to cell culture substrates, it is necessary to use a solvent that does not invade the surface of the cell culture substrates. For instance, in the case where plastic is used as a cell culture substrate and MMAC, MBAC, MHAC, and MAST are applied thereto, although MMAC and MBAC are easily soluble to acetone, acetone invades plastic surface. However, MMAC, MBAC, MHAC and MAST are scarcely soluble to n-hexane that does not invade plastic. Therefore, it is better to use ethanol that is a polar solvent and does not invade plastic surface. Because MMAC and MBAC are soluble to ethanol, they are used more easily than other polymers that need acetone, etc., and moreover, they can be easily air-dried after coating. In addition, the preferable concentration of MMAC, MBAC, MHAC, MAST, etc., used as an ethanol solution, etc., for coating treatments of the surface of cell culture substrates, is 2 µg/ml-1 mg/ml, particularly, 10-100 µg/ml. The coating treatment can be repeated 1-3 times according to desired degree of adhesion.

The immobilized preparation of cell adhesion proteins or peptides of the present invention means a preparation constructed by binding cell adhesion proteins or peptides to cell culture substrates coated with a hydrophobic binding-adsorptive polymer and immobilizing them. The bond is a covalent bond formed by the reaction between a functional group capable of reacting with proteins or peptides of a hydrophobic binding-adsorptive polymer and a reactive group of cell adhesion proteins or peptides. Examples of covalent bond include amide bond, thioamide bond, ester bond and thioester bond, described later, and amide bond is particularly preferable.

Examples of the reactive group of cell adhesion proteins or peptides include carboxyl, amino, mercapto, and hydroxyl groups of terminals or side chains of proteins or peptides.

As a method for reacting and binding functional groups, which can react to proteins or peptides, of a hydrophobic binding-adsorptive polymer to the reactive groups of cell adhesion proteins or peptides, a method for ordinary peptide synthesis can be used. For example, a carboxyl group at one side can react to an amino group, a mercapto group, or a hydroxyl group at another side in the presence of a condensing agent, and its reactive derivatives, such as acid halide, acid anhydride, and activated ester, can form covalent bonds, such as amide bond, thioamide bond, and ester bond. An amino group can react to a carboxyl group in the presence of a condensing agent, and its reactive derivative such as isocyanate as well, and form amide bond. A mercapto group and a hydroxyl group can react in the same manner to the carboxyl group described above in the presence of a condensing agent or to the reactive derivatives of a carboxyl group, and can form thioester bond or ester bond. In addition, an easily-cleavable and reversible protective group can be attached to the functional group or the reactive group to the extent that it can form a copolymer with the aforementioned self-polycondensation or hydrophobic linear skeleton.

As a cell adhesion protein, fibronectin (FN), collagen (Col), laminin (LN) and vitronectin (VN), etc., are exemplified.

Any peptides in the region relating to cell adhesion in the amino acid sequence of the cell adhesion proteins described above can be used as a cell adhesion peptide. The length of such peptides is 3-20, preferably 6-15, more preferably 6-12 amino acid residues.

As a peptide in the region relating to the cell adhesion of FN protein, a peptide having the specific RGD amino acid sequence which binds to an integrin receptor on a cell side is preferable, and as a specific sequence, Tyr-Ala-Val-Thr-Gly-Arg-Gly-Asp-Ser-Pro-Ala-Ser (FIB-1) (SEQ ID NO: 16) is exemplified.

Further, an α-chain G-domain peptide is also preferable as a peptide in the region relating to the cell adhesion of LN protein, which is considered to be especially important to the functional expression of epithelial cells, vascular endothelial cells, muscle cells, neural cells (neurons), etc., and for instance, Arg-Lys-Arg-Leu-Gln-Val-Gln-Leu-Ser-Ile-Arg-Thr (AG73) (SEQ ID NO: 1), Leu-Gln-Gln-Arg-Arg-Ser-Val-Leu-Arg-Thr-Lys-Ile (AG73T) (SEQ ID NO: 2), Thr-Leu-Gln-Leu-Gln-Glu-Gly-Arg-Leu-His-Phe-Met (AG76.8) (SEQ ID NO: 17), Thr-Leu-Gln-Leu-Gln-Glu-Gly-Arg-Leu-His-Phe-Nle (AG76.8X) (SEQ ID NO: 18), Val-Lys-Thr-Glu-Tyr-Ile-Lys-Arg-Lys-Ala-Phe-Met (AG81.2) (SEQ ID NO: 3), Val-Lys-Thr-Glu-Tyr-Ile-Lys-Arg-Lys-Ala-Phe-Nle (AG81.2X) (SEQ ID NO: 4), Lys-Asn-Arg-Leu-Thr-Ile-Glu-Leu-Glu-Val-Arg-Thr (A2G73) (SEQ ID NO: 5), Lys-Pro-Arg-Leu-Gln-Phe-Ser-Leu-Asp-Ile-Gln-Thr (A3G72) (SEQ ID NO: 6), Lys-Phe-Leu-Glu-Gln-Lys-Ala-Pro-Arg-Asp-Ser-His (A4G73) (SEQ ID NO: 19), Gly-Glu-Lys-Ser-Gln-Phe-Ser-Ile-Arg-Leu-Lys-Thr (A4G78) (SEQ ID NO: 20), Thr-Leu-Phe-Leu-Ala-His-Gly-Arg-Leu-Val-Phe-Met (A4G82) (SEQ ID NO: 7), Thr-Leu-Phe-Leu-Ala-His-Gly-Arg-Leu-Val-Phe-Nle (A4G82X) (SEQ ID NO: 8), Gly-Pro-Leu-Pro-Ser-Tyr-Leu-Gln-Phe-Val-Gly-Ile (A5G71) (SEQ ID NO: 9), Arg-Asn-Arg-Leu-His-Leu-Ser-Met-Leu-Val-Arg-Pro (A5G73) (SEQ ID NO: 10), Arg-Asn-Arg-Leu-His-Leu-Ser-Nle-Leu-Val-Arg-Pro (A5G73X) (SEQ ID NO: 11), Leu-Val-Leu-Phe-Leu-Asn-His-Gly-His-Phe-Val-Ala (A5G77) (SEQ ID NO: 12), Leu-Val-Leu-Phe-Leu-Asn-His-Gly-His (A5G77f) (SEQ ID NO: 13), etc., which are derived from mouse LN, and Lys-Asn-Ser-Phe-Met-Ala-Leu-Tyr-Leu-Ser-Lys-Gly (hA3G75) (SEQ ID NO: 21), Gly-Asn-Ser-Thr-Ile-Ser-Ile-Arg-Ala-Pro-Val-Tyr (hA3G83) (SEQ ID NO: 15), etc., which are derived from human LN, are exemplified. The cell adhesion peptides are available through ordinary methods for synthesizing peptides.

The immobilized preparations of cell adhesion proteins or peptides can be prepared by the process comprising: coating a hydrophobic bonding-adsorptive polymer to cell culture substrates in advance by the method described above, to coat the substrates; reacting the functional group, which can react to a reactive group of cell adhesion proteins or peptides, of the polymer to the reactive group of proteins or peptides.

The reaction may be conducted according to ordinal methods for peptide bonding, for example, by conducting a reaction between MMAC, MAST, etc., coated in advance on cell culture substrates and cell adhesion peptides at between room temperature and 50° C., preferably 37° C., in neutral or alkaline state, which means at pH 7-11, for 10 minutes to 48 hours, to form covalent bond and achieve immobilization.

Further, the immobilized preparations of cell adhesion proteins or peptides can be prepared also by the process comprising: a functional group, which can react to proteins or peptides, of hydrophobic binding-adsorptive polymers reacts to a reactive group of cell adhesion proteins or peptides in advance; the reactant is coated to cell culture substrates. The immobilization of cell adhesion substances is conducted in the two-step treatment comprising coating of a hydrophobic binding-adsorptive polymer on cell culture substrates, and the immobilization reaction of proteins or peptides. However, by the use of the reactant obtained by reacting a hydrophobic binding-adsorptive polymer and cell adhesion proteins or peptides in advance (herein after referred to as "pseudomatrix"), the preparation can be conducted in a one-step treatment comprising just coating of a pseudomatrix. Followings are examples of advantages concerning pseudomatrices:

a) coating process to wells becomes simplified, and it is industrially advantageous.

b) by the use of print technology, application is easily extended to substances other than culture wells by spraying, therefore, various kinds of base materials can be diverted to culture substrates.

c) it becomes possible to print a part for cell adhesion, and to design (arrange) the way of coculturing various cells. An artificial tissue can be constructed just like an IC circuit is designed.

d) pseudomatrices can be coated not only by a method comprising dilution with a culture medium, and adsorption/immobilization onto the surface of wells, but also by a method comprising, for example, dilution with 50% ethanol. In this method, salts is not deposited after air-drying, and the shelf life at high temperature is excellently improved.

Reaction between a hydrophobic binding-adsorptive polymer and cell adhesion proteins or peptides, and a method of coating a produced pseudomatrix to cell adhesion substrates can be performed according to the method described above.

With regard to a reaction between a functional group, which can react to proteins or peptides, of a hydrophobic binding-adsorptive polymer and a reactive group of cell adhesion proteins or peptides, it is possible to let reactive groups of cell adhesion proteins or peptides completely occupy all functional groups of the polymer (the occupation by cell adhesion proteins or peptides is 100%), however, preferably the occupancy is 1-50%, more preferably 5-15%. When the occupancy increases, the adsorption degree of pseudomatrix to culture substrates decreases due to water-solubility of proteins or peptides, and the solubility to organic solvents such as ethanol decreases as well, the deposition will easily occur consequently. In addition, even if increasing the density of proteins or peptides, it will be in vain unless the density of receptors of cells increases, and is economically undesirable.

The immobilized peptides prepared by the present invention, in particular, shows no changes in its cell adhesion activity even if it is left still at neutral pH, 37° C. for 4 days and is extremely stable. This fact shows that the immobilized preparation of cell adhesion peptides can be used as various culture substrates, and that as to its performance, it has an activity sufficiently parallel to that observed in the case where FN, a representative adhesion protein, is directly immobilized on cell culture substrates. In addition, though the concentration of cell adhesion peptides is conventionally necessary to be at least 2.5 mg/ml in order to immobilize peptides directly to cell culture substrates, the concentration is sufficient at 0.25 mg/ml or less according to the preparation method of the present invention, and even if the amount of peptide used is 1/10-1/100 or less in comparison with that of conventional methods, the immobilization can be conducted efficiently and with a good reproducibility by the present invention.

Further, when cell adhesion proteins are directly immobilized on cell culture substrates, the substrates are coated usually at the concentration from 5 to 10 μg/ml, and this does not cause a problem in an usual static culture. However, in the case of a stretching culture on silicone rubber, cells can be very easily detached because of its weak adsorption by hydrophobic binding between proteins and silicone rubber. The method of the present invention concerning the adsorption to silicone rubber through MMAC, etc., is effective means for preventing this kind of troubles.

Subsequently, artificial tissues can be prepared by seeding and culturing desired cells on an immobilized preparation of cell adhesion proteins or peptides. A method for constructing such artificial tissues is not particularly limited as long as it is a method wherein desired cells are seeded and cultured on an immobilized preparation of cell adhesion proteins or peptides. Once desired cells are seeded on an immobilized preparation, the seeded cells adhere and spread thereafter rapidly. Though there is no need to add serum to the culture medium particularly, the adherence and spreading are further promoted when serum is added at a low concentration, about 1% (in an usual cell culture, it is used at the concentration of about 10%).

As the desired cells, epithelial cells, endothelial cells, mesenchymal cells, etc., are exemplified. More specifically, examples of the epithelial cells include epidermal cells, corneal epithelial cells, alveolar epithelial cells, mucosal epithelial cells of digestive system, renal glomerular epithelial cells and hepatic parenchymal cells; examples of the endothelial cells include renal glomerular ciliated cells, vascular endothelial cells, pulmonary arterial vascular endothelial cells, placental venous vascular endothelial cells and aortic endothelial cells; examples of the mesenchymal cells include muscle cells, adipocytes, glial cells, Schwann cells and neural cells (neuron).

As for an artificial tissue (including an artificial organ) of human, etc., formed on cell adhesion proteins or peptides, any tissue which contains cell layers and a basement membrane just beneath the cell layers can be used. Specific examples include artificial tissues such as artificial epidermal tissues, artificial corneal epithelial tissues, artificial alveolar epithelial tissues, artificial respiratory epithelial tissues, artificial renal glomerular tissues, artificial hepatic parenchymal tissues, and artificial vascular endothelial tissues, and artificial organs such as artificial blood vessels, artificial lungs, artificial livers, artificial kidneys, artificial skins and artificial corneas.

Besides, the artificial tissues formed by seeding and culturing desired cells on an immobilized preparation of cell adhesion proteins or peptides can attach to the surface of a cell culture substrate, irrespective of kinds or materials of the cell culture substrates, because a hydrophobic binding-adsorptive polymers binds to the surface of the cell culture substrates by hydrophobic bond, but not by chemical bond. In addition, the artificial tissues can be physically exfoliated from the surface of the cell culture substrates when desired. The exfoliated artificial tissues are much more versatile, since they can be transplanted with holding the basement membrane structure. Their application examples include artificial microvessels with the inside diameter less than or equal to 3 mm, and human implantable artificial tissues. In particular, tissues and organs in which epithelial and endothelial tissues exist contiguously, such as artificial glomeruli, artificial livers, and artificial alveoli, are preferably exemplified.

Good results cannot be expected for a method wherein cells are directly seeded on the surface of cell culture substrates, which serve as a mechanical support structure for the preparation of tissues and organs, or the regeneration of tissues in vitro, because it is difficult to avoid the phenomenon of cell detachment for a long time, even if the surface of cell culture substrates is treated to become more hydrophilic. By contrast, the cell culture substrates coated with a hydrophobic binding-adsorptive polymer obtained by the present invention can allow cells to adhere efficiently and with an excellent reproducibility, and can significantly improve the results because of the method wherein cells are seeded on the surface via linkers. Although in a such case there is an alternative method of directly coating LN and FN, the method of the present invention is more effective, Otherwise, the cells also come to detach gradually from the surface of cell culture substrates. For example, by the commercially available "stretching cell culture apparatus", the stretching stimulus is periodically loaded to a uniaxial direction, and the morphological changes of cells caused by forced stretching stimuli in a state nearly in vivo can be observed. In this case where a silicone well (a well made from silicone rubber) coated with the polymer of the present invention is used as a silicone well used for the apparatus, the cells do not detach from the culture substrate and the cell observation can be conducted, even after stretching stimuli are loaded.

Further, a substance having cell adhesion activity can be immobilized on a flexible/deformable material by the present invention. For instance, print-wirings or IC circuits are constructed on flexible plastics nowadays. The present invention is useful for disposing cells like a circuit diagram by immobilizing cell adhesion proteins or peptides as a linker after coating MMAC, MBAC, MAST, etc., on the material described above with printing technology, or by directly immobilizing proteins or peptides, which have been bound to reactive polymers in advance, on plastic.

In addition, the present invention makes it possible to immobilize a substance having cell adhesion activity on a material to which cells are difficult to adhere (polymers, inorganic materials, metals, etc., with strong hydrophobicity or smooth surface). For example, hollow fibers of artificial blood vessels or artificial heart lungs made from synthetic polymers are made to achieve the most hydrophobic and smoothest surface without asperity in order to prevent platelets from adhering and forming clots. Even if these materials are applied, clots are inclined to form and clog in brain and pulmonary microvessels, resulting in a medical problem. Though the prevention of clot formation has been attempted by heparin coating, the clot formation is still hard to be prevented. For dealing with this problem, a method wherein the synthetic polymers are coated with reactive polymers such as MMAC, MBAC, MAST, etc., to immobilize heparin, and a method wherein the plastic surface is covered with vascular endothelial cells, are considered to be effective. Vascular endothelial cells have a function to prevent clot formation. It can be applied for the purposes of the immobilization of heparin as well as the immobilization of linkers having cell adhesion activity, and seeding of vascular endothelial cells to cover plastic surface.

Collagen fibrils, a useful cell adhesion substrate, involve integrin receptors in adhesion. However, it is not in a tissue construction model under normal conditions, but in a pathological model envisioning clinical conditions in mind, that integrin works for the adhesion of epithelial cells, endothelial cells, etc. Because the basement membrane is present just beneath the cell layers, the involvement of integrin is not desirable (suitable). The desirable tissue construction is one under a condition wherein syndecan, which usually participates in vivo, works. However, it is actually difficult to coat the surface of collagen fibrils with laminin, a main component of basement membrane. Instead, if collagen fibrils are coated with adhesion peptides in LN α-chain G-domain by using the method shown by the present invention, it becomes possible to construct tissues wherein syndecan works instead of integrin.

Cellulose is an industrial material that is inexpensive, has sufficient strength and semipermeable membrane property, can be formed into various shapes, and is easy to fit into living bodies. However, because it does not have functional groups necessary for cell adhesion, it is necessary to coat it with cell adhesion molecule for the use of a base material of artificial organs or cell cultures. However, the coating efficiency and the residuality of coated materials are not excellent. Consequently, cellulose has been used as a suspension culture substrate for non-adherent cells, and has not been suitable as a culture substrate for adhering cells. Herein exemplified MMAC, MBAC, MHAC (hydrophobicity increases in this order) can be applied to the material thus described due to high flexibility of their methylene groups, and further, by changing side chains to methoxy, butoxy, hexyloxy groups for increasing hydrophobicity, the coating by the present invention can be optimized, for instances, on the lumen and outer surface of a tube formed like a hollow fiber, and as a result, they can be used as base materials for cell adhesion.

The present invention can be applied to a substance other than polystyrene, which is usually used for cell culture. For example, by conducting a treatment for immobilizing cell adhesion proteins or peptides on the surface of implantable plastics such as artificial blood vessels and artificial lens used in medical treatment, an environment where in patients' cells easily adhere can be developed, and the reduced burden of patients can be expected.

The present invention will be more specifically described in the following with reference to Examples, but the technical scope of the invention will not be limited to these Examples.

Example 1

Coating of Silicone Wells

A silicone well coated with MMAC was obtained by pouring 0.5 ml of ethanol solution of 50 μg/ml of MMAC (ISP, International Specialty Products, USA) into a silicone well with a groove of 20 mm×20 mm×10 mm, absorbing excess solution, and conducting air-drying.

Whether the silicone well is coated with MMAC or not can be confirmed by, as described in Examples later, for example, the immobilizing cell adhesion proteins or peptides after coating the silicone well with MMAC, and seeding and culturing cells thereon.

Example 2

Static Culture of T2 Cells

Into the silicone wells coated by the method described in Example 1, 10 µg/ml of cell adhesion protein solution of fibronectin (FN), laminin-1 (LN), dissolved in 0.1 M triethanolamine buffer solution of pH 8.8, or 0.25 mg/ml of cell adhesion peptide solution of FIB-1, AG73 was poured respectively, and the reaction was conducted for at least several hours at 37° C. to bind and immobilize these proteins or peptides having cell adhesion activity (see Example 6 described later for particulars of immobilization). Subsequently, alveolar type II epithelial cell (T2 cells) suspension was poured, $5 \times 10^4/cm^2$ per unit area, and the culture was started in a $CO_2$ culture apparatus.

When the cell adhesion proteins or peptides were immobilized, T2 cells proliferated well and the cell density increased without fail (FIG. 1). Based on this result it is understood that the immobilization reaction of cell adhesion proteins or peptides by any MMAC coating does not affect cytotoxicity.

In the figure, 1d, 2d and 3d mean the period of culture days, respectively.

Example 3

Stretching Culture of T2 Cells 1

Figure 2:
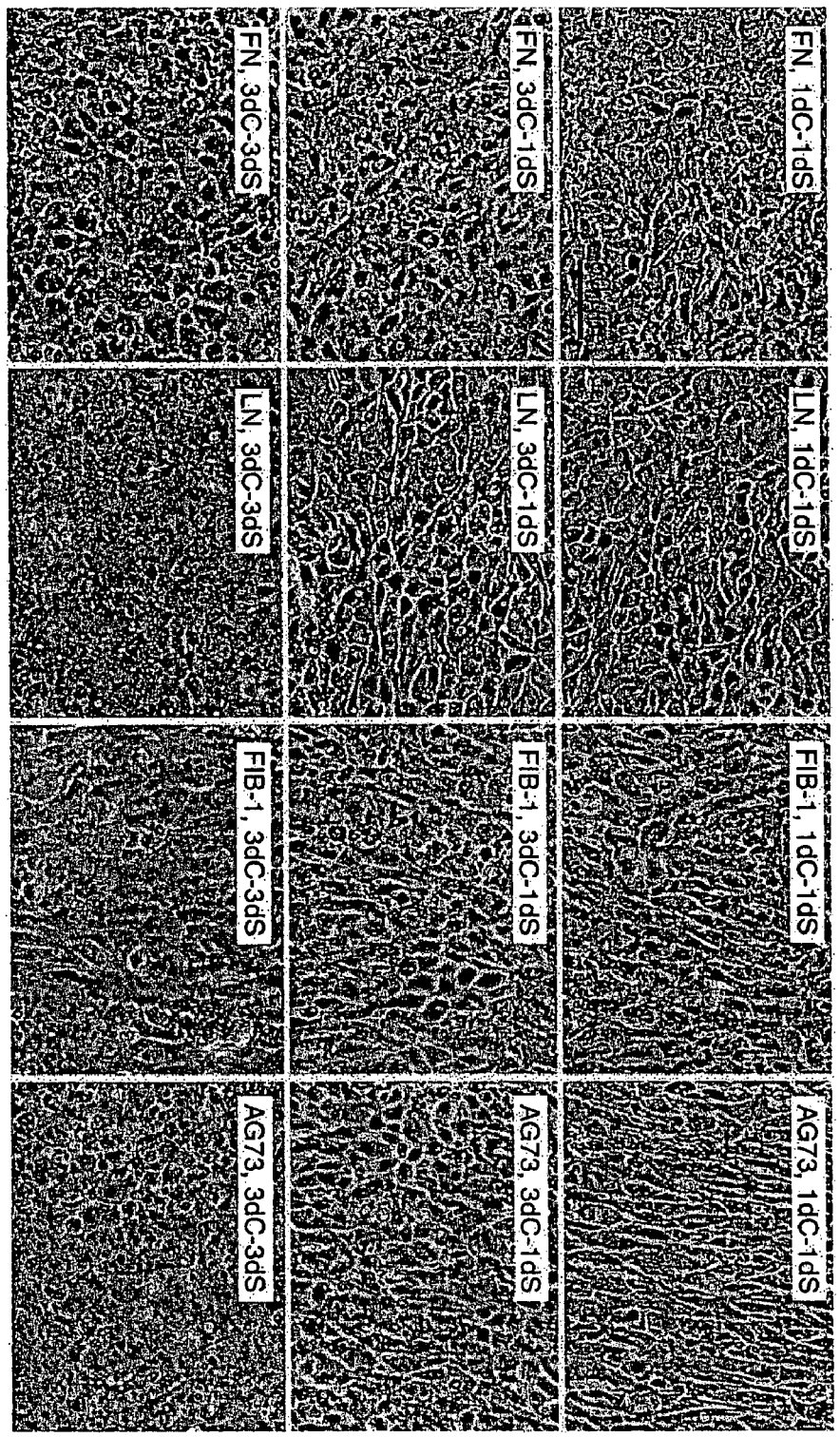
FIG. 2. is a set of phase contrast micrographs of alveolar epithelial tissues formed as a result of stretching culture of T2 cells on a silicone well wherein extracellular matrix proteins and cell adhesion peptides were immobilized by using MMAC.

T2 cells, $2 \times 10^5/cm^2$ per unit area, were seeded on the silicone well wherein the cell adhesion proteins or peptides were immobilized, which had been prepared in an almost same manner as that of Example 2, and static culture was conducted for 1 day. After confirming that the seeded cells confluently spread all over the culture face, horizontal cell stretching was forcibly started at the stretching degree of twenty five percents and at the frequency of 15 times per minute, by using cell culture stretching apparatus (Scholar Tec), and the culture was continued one more day. After the culture was finished, photographs of cell adhesion state were taken with a phase contrast microscope (FIG. 2, top 4 rows).

Though it is not very obvious in cases of the immobilized FN and LN (FN, 1dC-1dS, and LN, 1dC-1dS), in cases where cells were cultured while stretching forcibly on the immobilized FIB-1 and AG-73 cell adhesion peptides (FIB-1, 1dC-1dS, and AG-73, 1dC-1dS), it is clearly observed that T2 cells autonomically spread in an elongated shape to a direction perpendicular to the direction of forced stretching (vertical direction of photographs in FIG. 2) and orientated again, in order to reduce the effect of forced stretching as much as possible. The reason why the reorientation in the cases of immobilized FN or LN was not very clear in comparison to the above case is presumed as follows: because the adhesion between immobilized cell adhesion proteins and cells was strong enough to counter the power of forced stretching, there was no need to reorientate.

Example 4

Stretching Culture of T2 Cells 2

T2 cells, $5 \times 10^4/cm^2$ per unit area, were seeded on the silicone well wherein the cell adhesion proteins or peptides were immobilized, which had been prepared in an almost same manner as that of Example 2, and static culture was conducted for 3 days. T2 cells grew in a manner similar to that shown in FIG. 1, 3d (results are not shown because they are overlapping). Then, the cells were subjected to the same stimuli of forced stretching as in Example 1, and the culture was continued one more day. After the culture was finished, photographs of cell adhesion state were taken with a phase contrast microscope (FIG. 2, middle 4 rows) (FN, 3dC-1dS, LN, 3dC-1dS, FIB-1, 3dC-1dS, and AG-73, 3dC-1dS).

It is considered that T2 cells could adhere strongly to the immobilized cell adhesion proteins or peptides, and spread/proliferated during the 3-day static culture. Consequently, T2 cells did not reorientate as clearly as shown in the top of FIG. 2, even after cell stretching load was forcibly put for 1 day.

Example 5

Stretching Culture of T2 Cells 3

Forced stretching culture was conducted for 3 days in an almost same manner as stretching culture of Example 4. After the culture was finished, photographs of cell adhesion state were taken with a phase contrast microscope (FIG. 2, bottom 4 rows) (FN, 3dC-3dS, LN, 3dC-3dS, FIB-1, 3dC-3dS, and AG-73, 3dC-3dS).

By the 3-day forced stretching stimuli, the characteristics of T2 cells changed in a manner dependent on the immobilized cell adhesion proteins or peptides. In particular, when the cells were seeded on LN, an essential component of basement membrane structure present just beneath T2 cells in a living body, and on AG73, an adhesion peptide of LN, cubic type II epithelial cells changed into a shape like flat type I epithelial cells. In a living body, it is not a thick type II epithelial cell, but a flat type I epithelial cell that is subjected to repeated and most forced cell stretching in alveoli by breathing movement. The 3-day forced cell stretching suggests that type II epithelial cells differentiated into type I epithelial cells just like in a living body. FN is originally an extracellular matrix that gives cells stimuli for proliferation and migration. It would be due to this property of FN that the changes into a shape like type I epithelial cells were less observed on the immobilized FN and its adhesion peptide FIB-1 than on LN and AG73.

The forced cell stretching culture (stretching degree of twenty five percents) conducted in Examples 3 to 5 puts much more load on cells than at the stretching degree of ten percents, an usual degree of load was applied for the cell culture with the stretching apparatus described above. Therefore, when such a load was applied with the apparatus, the cells detach usually. With the use of the coated silicone well of the present invention, the cells proliferated well without detachment.

Example 6

Preparation of Immobilized Preparation of Cell Adhesion Proteins or Peptides All treatments are assumed to be aseptic treatments. First, in the case of cell adhesion proteins, 10 µg/ml of a hydrophobic binding-adsorptive polymer, such as MMAC and MAST, and in the case of peptides, 50 µg/ml of MMAC and MAST is dissolved in ethanol, the solution is filtered and poured by 50 µl each into a 96-well with no surface treatment for cell culture, leave it stand still for a while, and then MMAC etc., are removed and air-drying is conducted. Next, 10-20 µg/ml of cell adhesion protein or 0.25 mg/ml of peptide is dissolved in 0.1 M triethanolamine buffer, a solution of pH 8.8, and the mixture was poured by 50 µl each into a 96-well previously coated with MMAC etc. The solution is reacted overnight while humidifying in an incubator heated at 37° C. After the reaction finishes, the reaction liquid is absorbed, the remaining reaction solution is rinsed out with the medium, and the immobilized preparation of cell adhesion proteins or peptides is prepared. The preparation, as described in the following Examples, can be used for cell cultures as cell adhesion protein or peptide substrates.

Even the concentrations of cell adhesion proteins and peptides are adjusted to be one-fifth, which are, 2-4 μg/ml and 0.05 mg/ml respectively, no problems occurs in an usual cell culture.

When coating is conducted only with MMAC etc., cells can hardly adhere to the bottom surface of a 96-well because of the negative charge of carboxyl groups generated by hydrolysis of maleic anhydride.

Example 7

Adhesion of T2 Cells to Cell Adhesion Proteins, and Inhibition of Cell Adhesion by the Free Cell Adhesion Peptides Commercially available FN, LN and VN, usually used as cell adhesion proteins at cell culture, were coated to wells at the concentrations of 5 μg/ml, 10 μg/ml and 10 μg/ml, respectively. In case of Col I (collagen type I), Col I at the concentration of 100 μg/ml, dissolved in 1 mM HCl, was poured into a well, left stand still for a while, and then the solution was removed and air-drying was conducted, and rinsed with the medium, before use. Next, $6 \times 10^5$ cells/ml of alveolar type II epithelial cells (T2 cells) suspended in the serum-free DMEM medium was seeded by 100 μl each on a 96-well to which the extracellular matrix was coated, and cultured in a $CO_2$ incubator at 37° C. for 1 day. After the culture was finished, the cells were fixed with 100 μl of methanol for 5 minutes, and stained for 30 minutes with 50 μl of 0.4% crystal violet. Excessive staining was washed with water, then the number of cells adhered to FN, Col I, LN and VN, which had been coated to the wells, was counted based on the absorbance of cytoplasm (A595).

Figure 3:
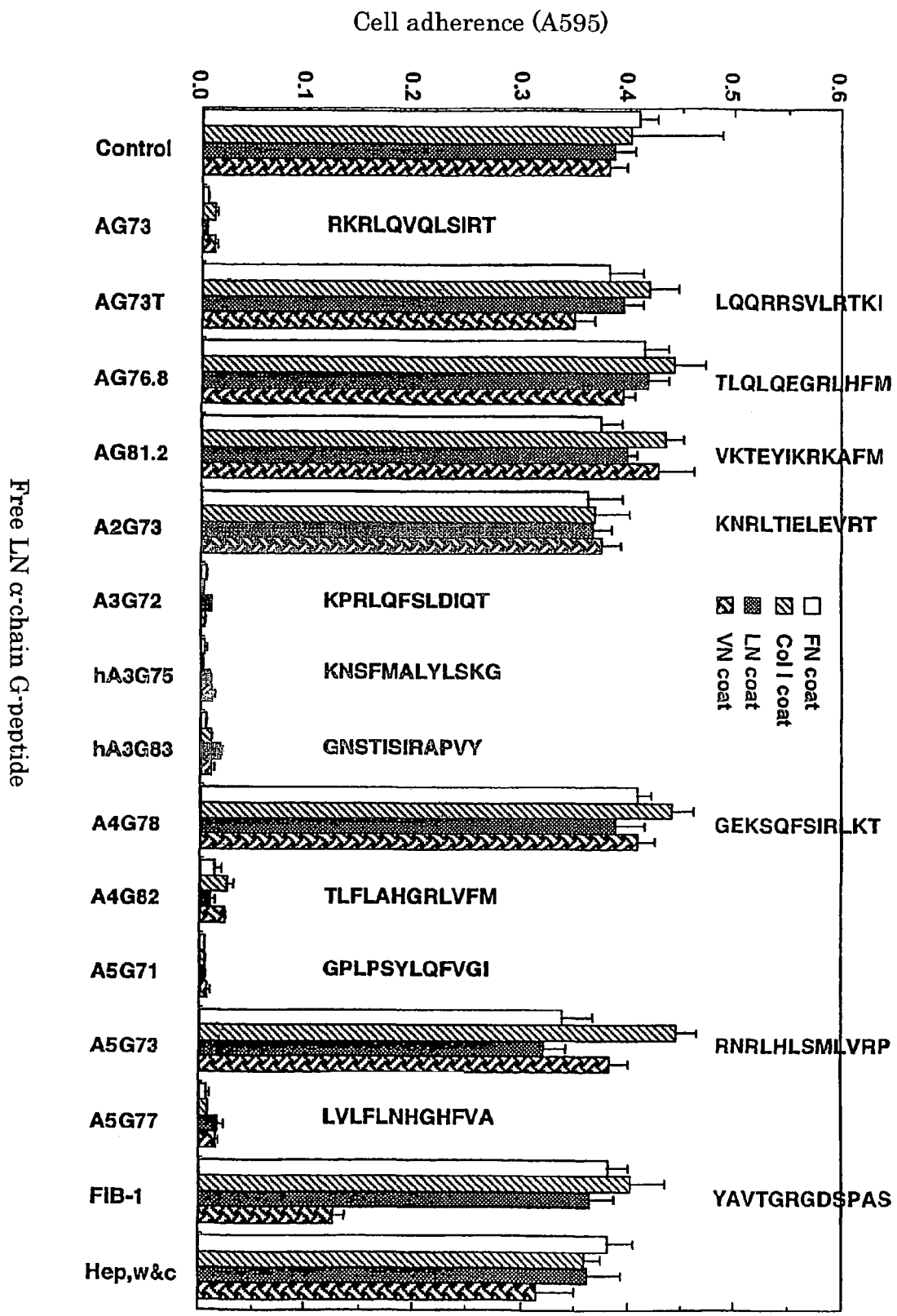
FIG. 3 is a graph showing that the adhesion of T2 cells to extracellular matrix proteins coated/immobilized in a well was inhibited by the free cell adhesion peptides.

On the other hand, among amino acid sequences of various LN molecules, the sequences that induce cell adhesion are known to be present. Several kinds of synthesized cell adhesion peptides were added at the concentration of 0.25 mg/ml, to the cell culture medium prepared in a manner similar to that described above. Then, the number of cells was counted in accordance with the method described above. The results are shown in FIG. 3.

Among the cell adhesion peptides, in particular, AG73, A3G72, hA3G75, hA3G83, A4G82, A5G71, and A5G77 peptides inhibited adhesion of T2 cells. It is understood that these peptides have a strong affinity to the cells, and therefore, the adhesion of T2 cells to FN, Col I, LN and VN was inhibited.

FIB-1 peptide is known as a peptide that inhibits the adhesion to FN (usually, 1 mg/ml or more is required). Even at a low concentration such as 0.25 mg/ml, where FIB-1 peptide does not exhibit inhibitory effect, the peptides described above exhibit the inhibitory activity. Some kinds of LN peptides, such as AG73, also exhibited the inhibitory activity at the concentration of 0.12 mg/ml.

Example 8

Adhesion of T2 Cells to the Immobilized Cell Adhesion Peptide Substrates, and Inhibition of Cell Adhesion by the Free Peptides T2 cells suspended in the serum-free DMEM medium at the concentration of $6 \times 10^4$ cells/100 μl were seeded in the well prepared according to the manner in Example 6, wherein cell adhesion peptides were immobilized, and cultured in a $CO_2$ incubator at 37° C. for 24 hours. Then, in accordance with the manner in Example 7, the cells were fixed with methanol, stained, and the absorbance was measured. Just before seeding the cells, the free peptides, the same kind as the cell adhesion peptides used for immobilization, were also added to the cell suspension, and the absorbance was measured after the culture in the same manner as described above. As to the case wherein FN was applied as a standard material, the measurement was conducted as well. The results are shown in FIGS. 4 and 5.

Figure 4:
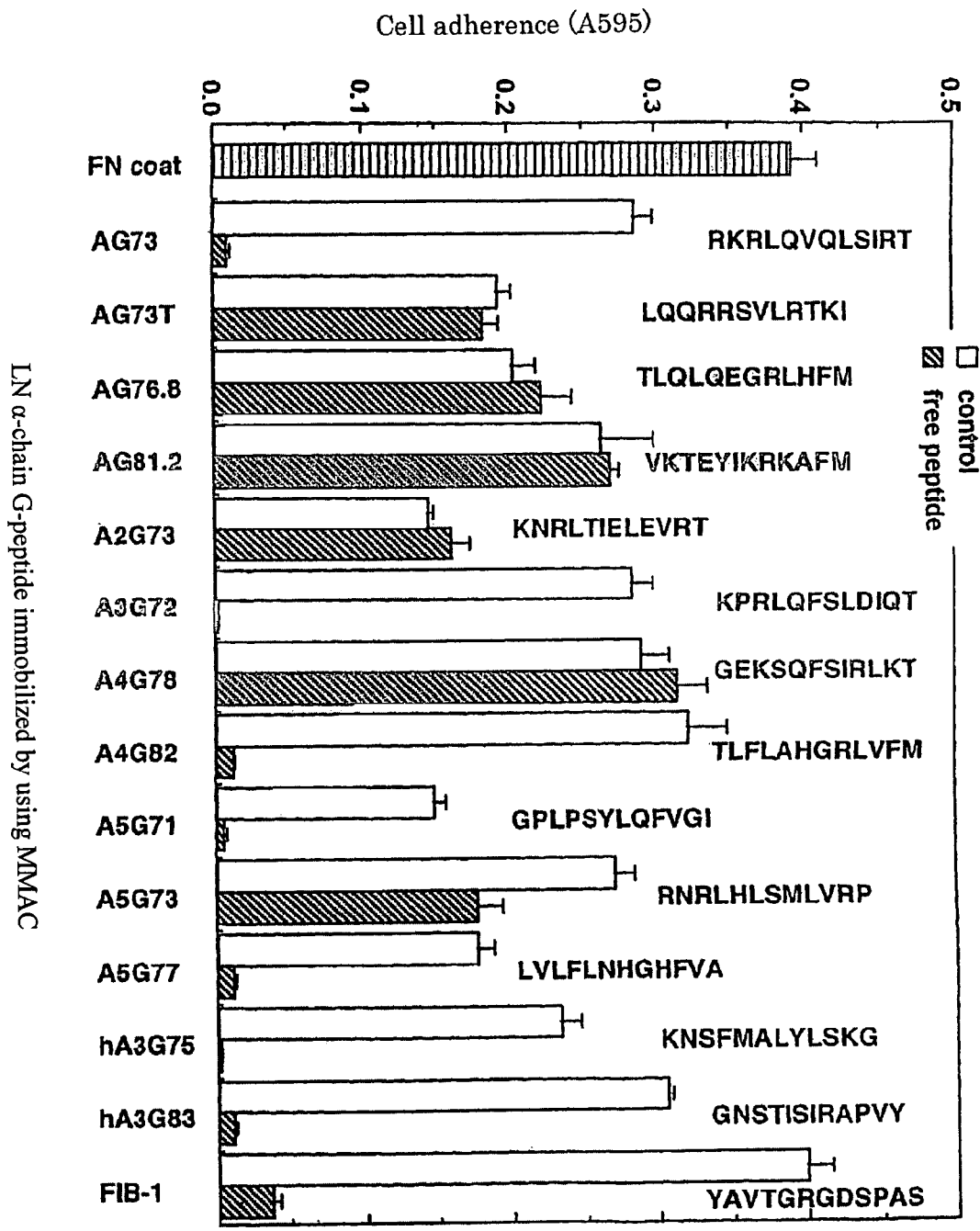
FIG. 4 is a graph showing the adhesion of T2 cells to the cell adhesion peptide substrates immobilized by using MMAC, and showing that the adhesion was competitively inhibited by the free cell adhesion peptides.
Figure 5:
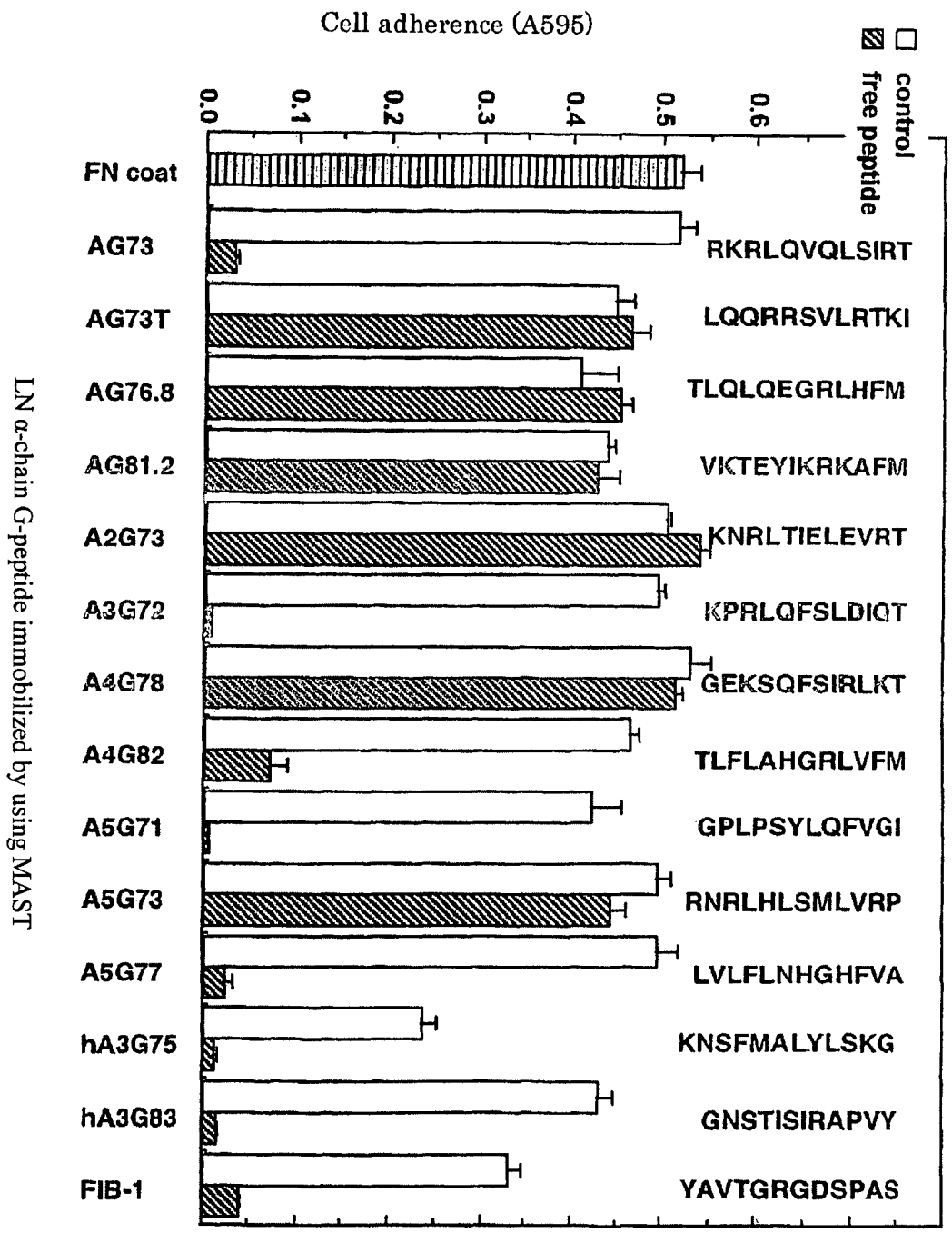
FIG. 5 is a graph showing the adhesion of T2 cells to the cell adhesion peptide substrate immobilized by using MAST of a hydrophobic binding-absorptive polymer, and showing that the adhesion was competitively inhibited by the free cell adhesion peptides.

FIGS. 4 and 5 show the results obtained with the use of wells prepared by using laminin α-chain G-peptides and FIB-1 peptide as cell adhesion peptides, and as a hydrophobic binding-adsorptive polymer, MMAC was used in FIG. 4, and MAST was used in FIG. 5. In FIGS. 4 and 5, "control" shows a culture wherein the immobilized cell adhesion peptides only existed, and "free peptide" shows a culture wherein the free peptides, the same kind as the immobilized cell adhesion peptides were coexistent at 0.25 mg/ml.

Concerning some cell adhesion peptides the amount of cell adhesion varies in accordance with the kinds of hydrophobic binding-adsorptive polymers used for immobilizing cell adhesion peptides. However, it does not change the fact that in both cases of MMAC and MAST, the cell adhesion was competitively inhibited by the free cell adhesion peptides. That is, the cells were adhered through the immobilized cell adhesion peptides. Therefore, when the free cell adhesion peptides coexisted, the immobilized cell adhesion peptides and the free cell adhesion peptides competed for the same adhesion receptor present on the cell surface, and as a result, the cell adhesion was inhibited. This suggests that there are the significant universality and reliability in this method wherein cell adhesion peptides are immobilized by using hydrophobic binding-adsorptive polymers and used as a foothold of cell adhesion.

In cases of AG73T, AG76.8, AG81.2, A2G73, A4G78, A5G73, it seems to be nonspecific adhesion prima facie, without competitive inhibition by their free cell adhesion peptides. However, this can be explained as follows: inhibition does not occur since the binding between adhesion receptors of the cells and the free cell adhesion peptides was weaker than that between the adhesion receptors and the immobilized cell adhesion peptides. Even for these cases, it is considered to be a specific adhesion through cell adhesion peptides and syndecan that belongs to heparan sulfate proteoglycan, an adhesion receptor on cell surface, because heparin treatment caused the inhibition of adhesion (see Example 10 and FIG. 7).

Example 9

Time Course of Cell Adhesion/Spreading of T2 Cells to the Immobilized Cell Adhesion Peptides Substrates, and Preparation of Artificial Tissues Culture was conducted by using the cell adhesion peptides immobilized on a well and T2 cells, for 1-24 hours according to the method in Example 8. Cell adhesion and spreading in the culture were observed with a differential interference (light) microscope. Results obtained by 1-, 6-, and 24-hour culture are shown in FIG. 6.

Figure 6:
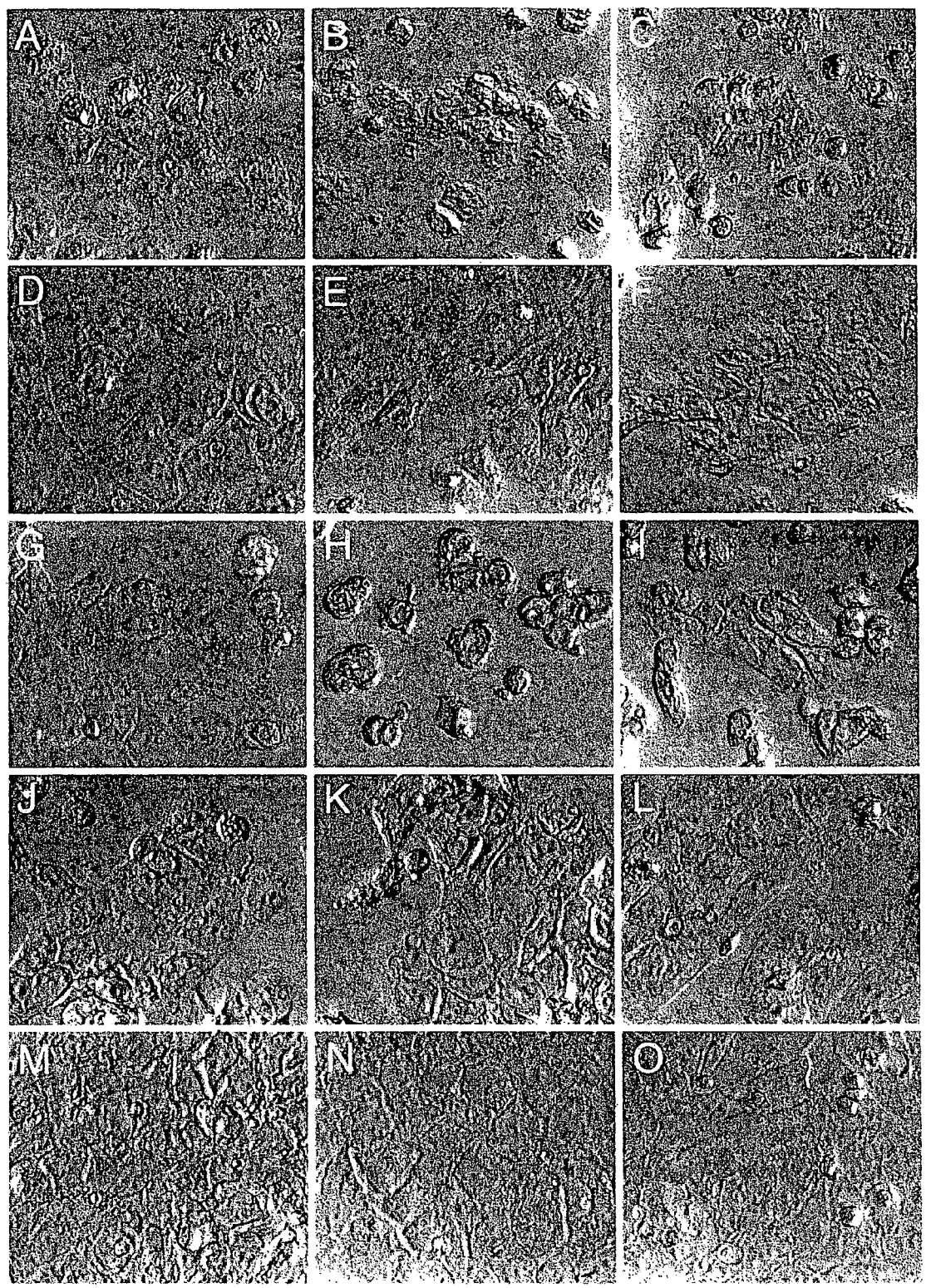
FIG. 6 is a set of photographs taken with a differential interference microscope showing the state of cell adhesion and spreading of T2 cells on the cell adhesion peptides immobilized by the use of MMAC.

FIG. 6 shows a set of micrographs taken with a differential interference microscope, at 1-hour (A to C), 6-hour (D to L), and 24-hour (M to O) cultures, conducted on the cell culture substrates on which T2 cells were seeded.

As cell adhesion peptides, AG73 was used in B, E and M, FIB-1 was used in C, L and O, A3G72 was used in F, A4G82 was used in G and N, A5G71 was used in H, A5G77 was used in I, hA3G75 was used in J, and hA3G83 was used in K; FN was used as a standard substance in A and D.

Though these cell adhesion peptide were not so much as FN, the cells also adhered on the cell adhesion peptides in 1 hour, and some cells started spreading. In 6-hour culture, those peptides were comparable to FN, and the cells were spreading on AG73, A3G72 and A4G82 peptides. On hA3G75 and hA3G83 peptides, there was a delay in spreading but sufficient cell adhesion was observed. In 24-hour culture, almost all cells had finished spreading on all of AG73, A4G82 and FIB-1, as in the case the cells were seeded on FN (not shown in figures).

Example 10

Figure 7:
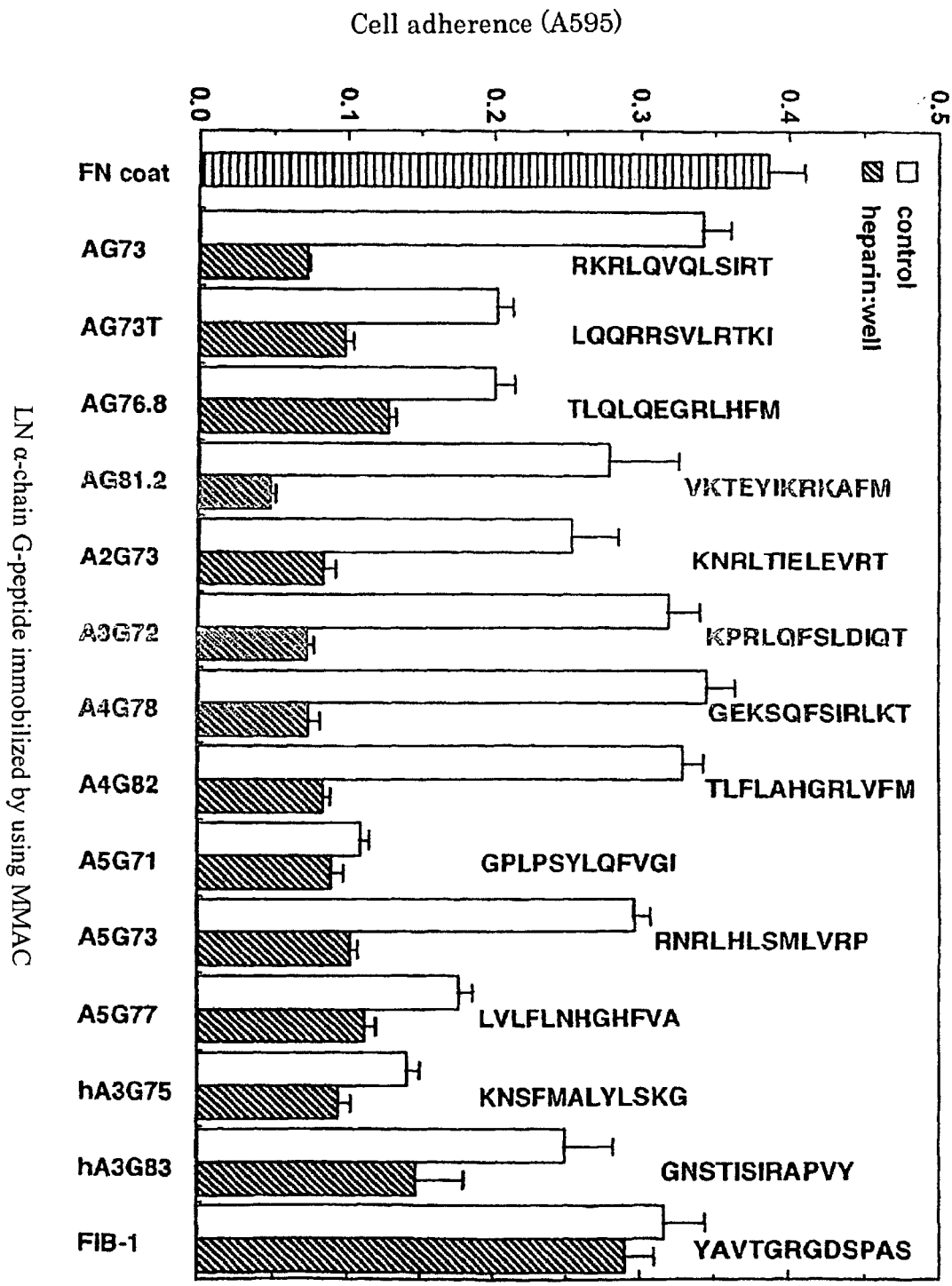
FIG. 7 is a graph showing that the adhesion of T2 cells to the cell adhesion peptide substrates immobilized by the use of MMAC was inhibited by heparin.

Inhibition of T2 Cell Adhesion to the immobilized Cell Adhesion Peptide Substrates by Heparin Treatment 100 μg/ml of heparin solution was poured into a well prepared according to the method in Example 6, wherein the cell adhesion peptides were immobilized, and the incubation was conducted for 2 hours. The heparin solution was removed after heparin bound to the immobilized cell adhesion peptides, and T2 cell suspension was seeded on the well. Results regarding the number of adhering cells after 24-hour culture are shown in FIG. 7.

It is theoretically shown that after the cell adhesion peptides first bind to heparin and are covered with heparin, the cell adhesion receptors having heparin-like sugar chain (heparan sulfate) present on the cell surface, in other words, syndecan, a protein that belongs to heparan sulfate proteoglycan, cannot bind to the cell adhesion peptides by using the sugar chain part of the heparan sulfate, thereby the cell adhesion is inhibited.

In case of the immobilized cell adhesion peptide derived from LN α-chain G-domain, the cell adhesion was inhibited almost entirely. This is understood that the intrinsic binding between syndecan, which has a sugar chain structure similar to that of heparin and is present on the cell surface, and the immobilized cell adhesion peptide was competitively inhibited because the immobilized peptides and heparin bound together by affinity.

Judging from the above, the counterpart to which AG73, AG73T, AG76.8, AG81.2, A2G73, A3G72, A4G78, A4G82, A5G73, A5G77, hA3G75, or hA3G83 bind is considered to be syndecan present on the cell surface. There is no inhibition in case of FIB-1 peptide. It is an established fact that a cell adhesion receptor involved in the binding to FN is integrin α5β1, and the binding site is the RGD amino acid sequence. Because the integrin is involved in the binding to FIB-1 peptide containing this sequence, it is reasonable that there occurs no inhibition caused by heparin. This fact also suggests the reliability of this Example.

Example 11

Figure 8:
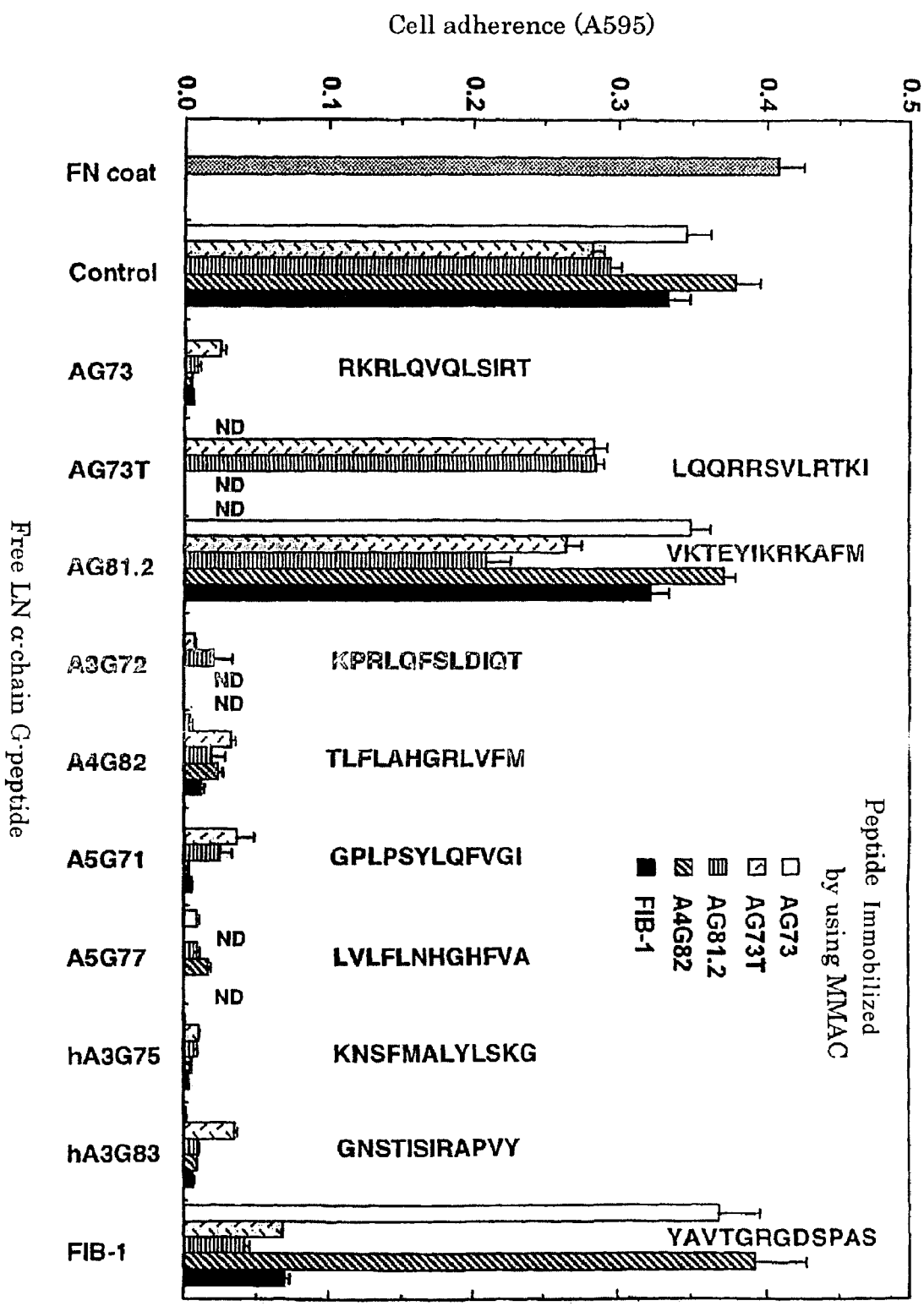
FIG. 8 is a graph showing that the adhesion of T2 cells to the immobilized cell adhesion peptide substrates could be competitively inhibited by free other peptides, bilaterally or unilaterally.

Inhibition of T2 Cell Adhesion by the Free Cell Adhesion Peptide Different from the Immobilized Cell Adhesion Peptide Substrate Results obtained by adding the free peptides different from the immobilized peptides when T2 cells were cultured on the immobilized peptide prepared according to the method in Example 7, were shown in FIG. 8.

When adding the free peptides that were the same as the immobilized peptides in the culture medium, the both (free and immobilized) peptides compete for syndecan of T2 cells and as a result, the cell adhesion is inhibited (see Example 7). So far, four types of syndecans are genetically known. Whether these syndecans are commonly owned or accommodated by each peptide, overlapping only by some degrees, otherwise mutually exclusive, was examined herein.

For example, when AG73 was immobilized, not only free AG73, but also A3G72, A4G82, A5G71, A5G77, hA3G75, hA3G83 inhibited the cell adhesion, and this suggests that receptors are commonly owned one another. However, AG81.2 and AG73T cannot inhibit it.

Further, when AG81.2 and AG73T were immobilized, free AG81.2 and AG73T could not competitively inhibit their immobilized peptide, or even if they can, only slightly. However, the cell adhesion was inhibited by the LN peptides described above.

This result indicates that the peptides commonly own (accommodate) the receptors one another. However, it is implied that the common ownership (accommodation) is not on equal terms but there is an order among peptides regarding affinity to the receptors. In other words, AG73, A3G72, A4G82, A5G71, A5G77, hA3G75, hA3G83>AG81.2, AG73T. AG73T is an artificial sequence constructed by shifting the amino acid sequence of AG73, and does not naturally exist.

The receptor of FIB-1 is not syndecan but a cell adhesion molecule called integrin. Binding between the integrin and FIB-1 is inhibited by LN peptides such as AG73, but not vice versa. In other words, when FIB-1 is immobilized, the inhibition is caused by the free LN peptides, but when AG73, etc. are immobilized, no inhibition occurred by the free FIB-1 at all. This indicates that the cell adhesion with syndecan has a priority over the cell adhesion with integrin. The advantage of immobilizing cell adhesion peptides of LN α-chain G-domain and using it as the cell adhesion substrates is also obvious in this respect.

Example 12

Binding Ability of Immobilized LN Cell Adhesion Peptides Based on Adhering and Binding Ability (Affinity) of T2 Cells to the Immobilized FIB-1 Peptide It is shown in FIG. 8 that free FIB-1 peptide not only competitively inhibited the cell adhesion of T2 cells to the immobilized FIB-1 peptide, but also inhibited the adhesion to AG73T and AG81.2 peptides. On the contrary, because free AG73T and AG81.2 peptides could not inhibit the cell adhesion to the immobilized FIB-1, the binding strength (affinity) of AG73T and AG81.2 peptides to T2 cells is lower than that of FIB-1 (see Example 12 and Table 1, classified into class C).

On the other hand, free AG73 and A4G82 peptides could inhibit the cell adhesion to the immobilized FIB-1 peptide, but free FIB-1 peptide could not inhibit the cell adhesion to the immobilized AG73 and A4G82 peptides. Therefore, it is obvious that the binding strength (affinity) of AG73 and A4G82 peptides to T2 cells is higher than that of FIB-1 (see Table 1, classified into classes AA and A), but it is unknown how high it is.

FIG. 8 suggests that when two kinds of the immobilized cell adhesion peptides, FIB-1 and AG73, are present simultaneously, free FIB-1 peptide could inhibit the adhesion if T2 cells adhered through FIB-1 peptide, but free FIB-1 peptide could not inhibit the adhesion if T2 cells adhered through AG73 peptide. Therefore, the amount of FIB-1 peptide was set at 0.25 mg/ml, and AG73 peptide was mixed therewith, while changing its concentration ratio, from 1/1.250 of FIB-1 in an amount which is 0.20 µg/ml, to ½ of FIB-1 in an amount which is 0.125 mg/ml, and the mixture was immobilized on a well wherein a hydrophobic binding-adsorptive polymer MMAC was coated. The amount of cell adhesion in the case where T2 cells were cultured under a serum-free condition for 1 day on the immobilized peptides is shown in FIG. 9, in comparison with the case where the culture was conducted on the immobilized FIB-1, which was set at 100%.

In a case of FIB-1:AG73=1:0.004, because T2 cells were still adherent through the immobilized FIB-1 peptide, free FIB-1 peptide inhibited the adhesion of T2 cells at the same level as the case where only FIB-1 was immobilized. However, in a case that the ratio of FIB-1:AG73 increased to 1:0.02, because T2 cells already transited to be adherent through the immobilized AG73 peptide, free FIB-1 peptide could no longer inhibit the cell adhesion. Because the mixing ratio at the transitional midpoint=0.01, its inverse, 100, shows the ratio of binding strength of AG73 to T2 cells versus FIB-1. Likewise, with regard to A3G72 and A4G82 peptides, because the mixing ratio at the transitional midpoint=0.1, their binding strength to T2 cells is 10 times as much as that of FIB-1. Based on this result, the binding strength of AG73, A3G72, A4G82 peptides to T2 cells are classified into classes AA and A, respectively (see Table 1).

Figure 9:
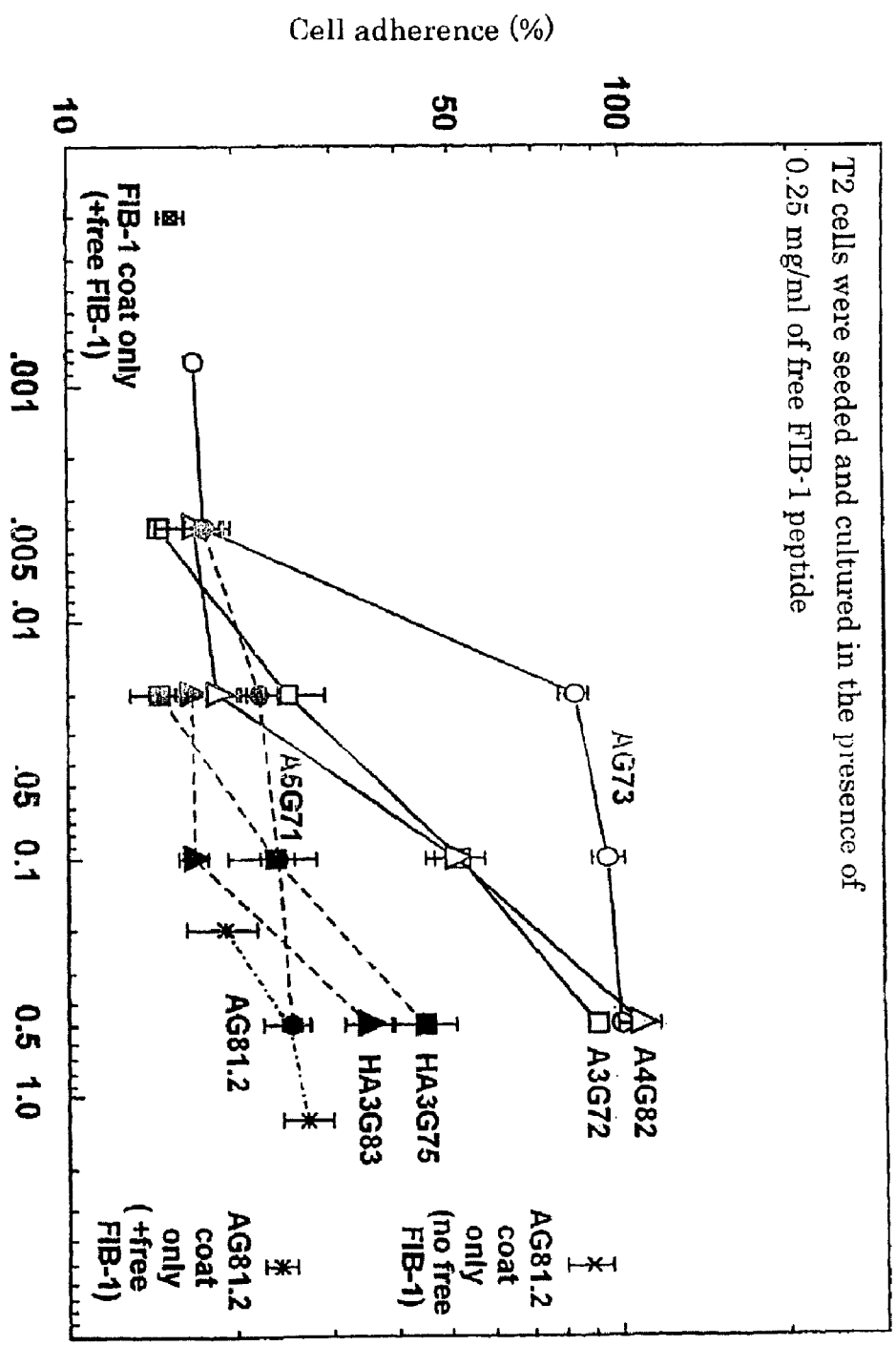
FIG. 9 is a graph showing that the affinity of immobilized cell adhesion peptides of LN varies widely from the similar to near 100-fold level as much as that of FIB-1 peptide, when adopting the cell adhesive strength (affinity) of T2 cells to the immobilized FIB-1 peptide as a standard.

In FIG. 8, free A5G71, A5G77, hA3G75, hA3G82 peptides could inhibit the cell adhesion to the immobilized FIB-1 peptide, however, their binding strength to T2 cells is classified into B, because the mixing ratio at the transitional midpoint was about 1 in FIG. 9 (see Table 1).

The method used in FIGS. 8 and 9 is extremely effective as a convenient method by which a relative order can be measured concerning to the binding strength (affinity) of cell adhesion peptides and the strength of cell adhesion can be considered quantitatively.

In Table 1, the classification is shown based on the results of the affinity (bonding/adhesion strength) between FIB-1 peptide containing RGD amino acid sequence of FN molecule, a binding site to integrin, and T2 cells: laminin α-chain G-domain peptides are classified into class AA, extremely strong binding/adhesion; class A, strong adhesion; class B, adhesion as the same degree as FIB-1; and class C, binding weaker than the described above.

TABLE 1

| Laminin α-chain G-peptides | Amino acid sequences | Inhibition degree of cell adhesion | | Binding strength to T2 cells | Comprehensive evaluation |
|---|---|---|---|---|---|
| | | Free peptide | Heparin | Ratio to FIB-1 | |
| AG73 | RKRLQVQLSIRT (SEQ ID NO: 1) | +++ | +++ | 100 | AA |
| AG73T | LQQRRSVLRTKI (SEQ ID NO: 2) | No | + | | C |
| AG76.8 | TLQLQEGRLHFM (SEQ ID NO: 17) | No | + | | C |
| AG81.2 | VKTEYIKRKAFM (SEQ ID NO: 3) | No | ++ | <1 | C |
| A2G73 | KNRLTIELEVRT (SEQ ID NO: 5) | No | ++ | | C |
| A3G72 | KPRLQFSLDIQT (SEQ ID NO: 6) | +++ | +++ | 10 | A |
| A4G78 | GEKSQFSIRLKT (SEQ ID NO: 20) | No | +++ | | C |
| A4G82 | TLFLAHGRLVFM (SEQ ID NO: 7) | +++ | +++ | 10 | A |
| A5G71 | GPLPSYLQFVGI (SEQ ID NO: 9) | +++ | No | <1 | B |
| A5G73 | RNRLHLSMLVRP (SEQ ID NO: 10) | + | ++ | | C |
| A5G77 | LVLFLNHGHFVA (SEQ ID NO: 12) | +++ | + | | B |
| hA3G75 | KNSFMALYLSKG (SEQ ID NO: 21) | +++ | + | 2 | B |
| hA3G83 | GNSTISIRAPVY (SEQ ID NO: 15) | +++ | + | 1-2 | B |
| FIB-1 | YAVTGRGDSPAS (SEQ ID NO: 16) | ++ | No | (1) | B |

AA: extremely strongly binding/adhering
A: strongly binding/adhering
B: intermediately binding/adhering (as the same degree as FIB-1 peptide)
C: more weakly binding/adhering than FIB-1 peptide Example 13

Preparation of Pseudomatrix 200 mg each of hydrophobic binding-adsorptive polymer, MBAC, MAST or MMAC were dispersed into water, and 1 N NaOH solution was added little by little to dissolve them completely. 50 mg of WSC (1-ethyl-3-(3-dimethylamino propyl)carbodiimide, hydrochloride) was added to the resulting solution, and the reaction was conducted for 2 hours. Subsequently, 20 mg of peptide was added, and the reaction was continued with stirring for 2 hours at room temperature. After the reaction was finished, the reactant was subjected to dialysis with water to remove alkaline and low molecules, and then freeze-dried to prepare a pseudomatrix of interest.

Example 14

Adhesion of T2 Cells to the Immobilized Pseudomatrix, and the Competitive Inhibition of Cell Adhesion by the Free Peptides-1

Figure 10:
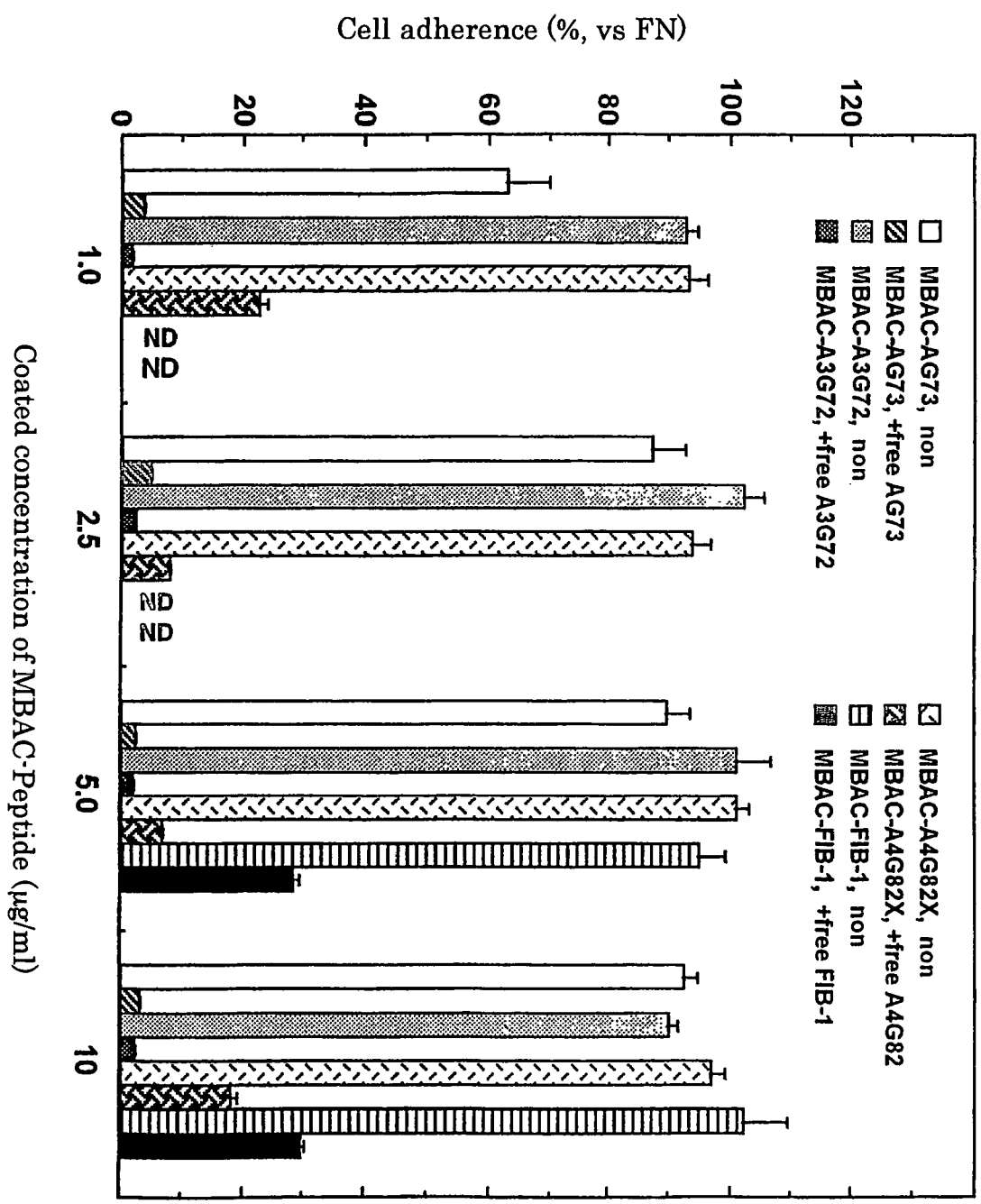
FIG. 10 is a graph showing the adhesion of T2 cells to pseudomatrix MBAC-peptides diluted to the concentration of 1-10 μg/ml in the serum-free medium and adsorbed/immobilized on wells, and showing that the adhesion was competitively inhibited by the free cell adhesion peptides.

Each pseudomatrix prepared in Example 13 to which cell adhesion peptide was bound (MBAC-peptide) was diluted in DMEM medium to the concentration of 1-10 μg/ml, and the resultant solution was poured into a 96-well by 100 μl each, and left still overnight in a $CO_2$ incubator to be adsorbed and immobilized on the wells. Non-adsorbed MBAC-peptides were removed by rinsing well with DMEM medium. Next, T2 cells suspended at the concentration of $6\times10^5$ cells/ml were seeded in the serum-free DMEM by 100 μl each. After 1-day serum-free culture, T2 cells were fixed with 100 μl of methanol for 5 minutes, and stained with 50 μl of 0.4% crystal violet for 30 minutes. Excessive staining was washed with water, and the number of adhering cells was counted based on the absorbance of cytoplasm (A595). The results are shown in FIG. 10.

In all measurements excluding the case of 1 μg/ml of MBAC-AG73, the similar level of cell adhesion ability as in the case where FN (fibronectin) was directly coated was exhibited by MBAC-AG73, -A3G72, -A4G82X, -FIB-1. In addition, because the cell adhesion was competitively inhibited by the free cell adhesion peptide, T2 cells are considered to adhere by the specific binding through cell adhesion peptides bound to MBAC. The fact that the adhesion of T2 cells to MBAC-A4G82X was inhibited by free A4G82 peptide indicates that even if Met residue at C-terminal is replaced by Nle residue, it has the same function with regard to cell adhesion.

Example 15

Adhesion of T2 Cells to the Immobilized Pseudomatrix, and the Competitive Inhibition of Cell Adhesion by the Free Peptides-2

Figure 11:
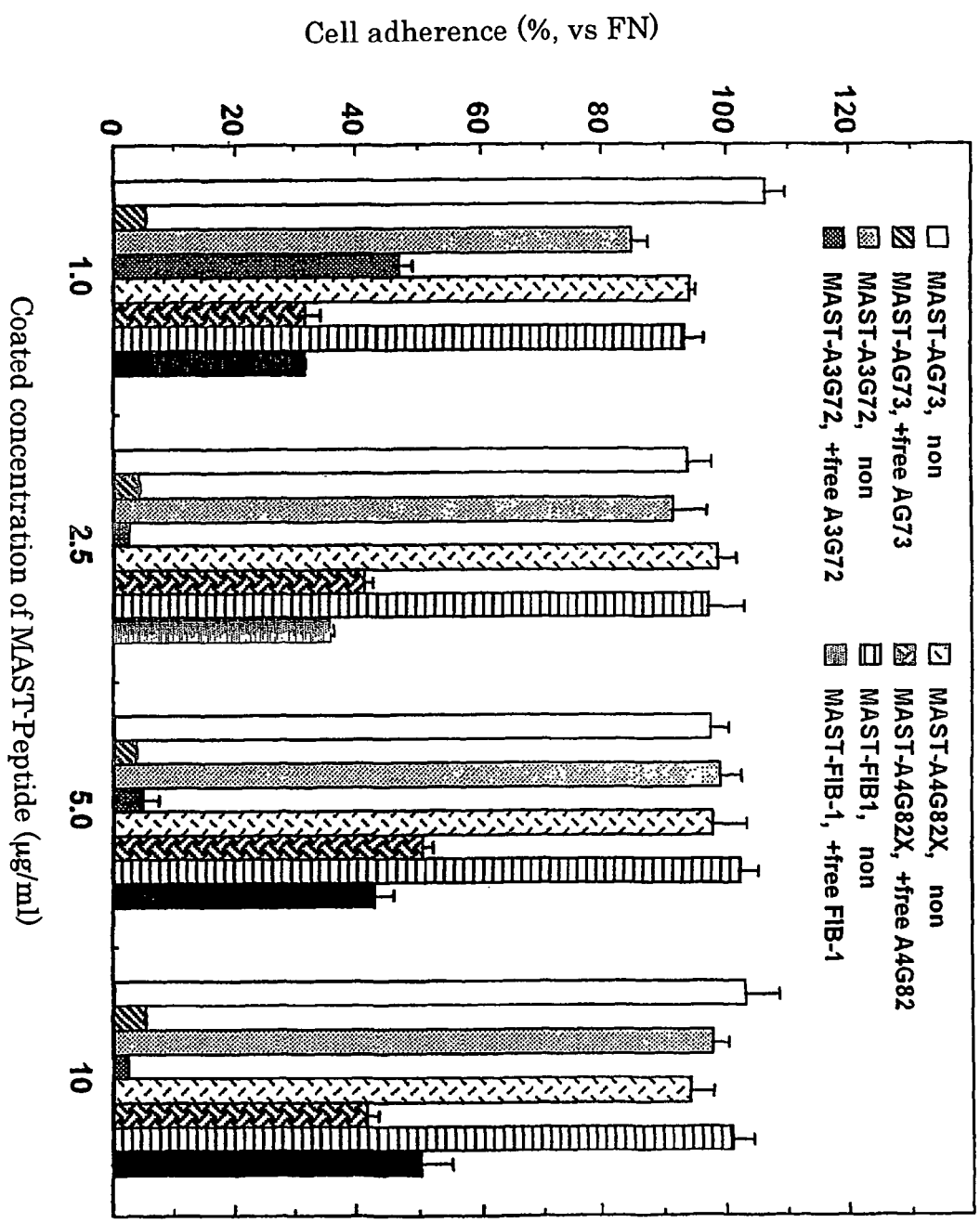
FIG. 11 is a graph showing the adhesion of T2 cells to pseudomatrix MAST-peptides diluted to the concentration of 1-10 μg/ml in the serum-free medium and adsorbed/immobilized on wells, and showing that the adhesion was competitively inhibited by the free cell adhesion peptides.

In the same manner as in Example 14, each pseudomatrix prepared in Example 13 to which cell adhesion peptide was bound (MAST-peptide) was adsorbed and immobilized on a 96-well, and T2 cells were seeded and cultured thereon. The results are shown in FIG. 11.

In all measurements ranging from 1-10 μg/ml, MAST-AG73, -A3G72, -A4G82X, -FIB-1 exhibited the same level of cell adhesion ability as in the case where FN was directly coated. In addition, though the cell adhesion was competitively inhibited by the free cell adhesion peptide, the degree is lower than the case of MBAC-peptide. It is considered that this is because the specific binding between T2 cells and MAST-peptide is stronger than that between T2 cells and MBAC-peptide. The fact that the adhesion of T2 cells to MAST-A4G82X was inhibited by free A4G82 peptide indicates that even if Met residue at C-terminal is replaced by Nle residue, it has the same function with regard to cell adhesion.

Further, even if a polymer-peptide (pseudomatrix) adsorbed/immobilized on a well is rinsed with DMEM during 2-4 days, there is no influence on the amount of cell adhesion. This indicates that the binding between a well and a pseudomatrix is sufficiently strong and stable.

Example 16

Figure 12:
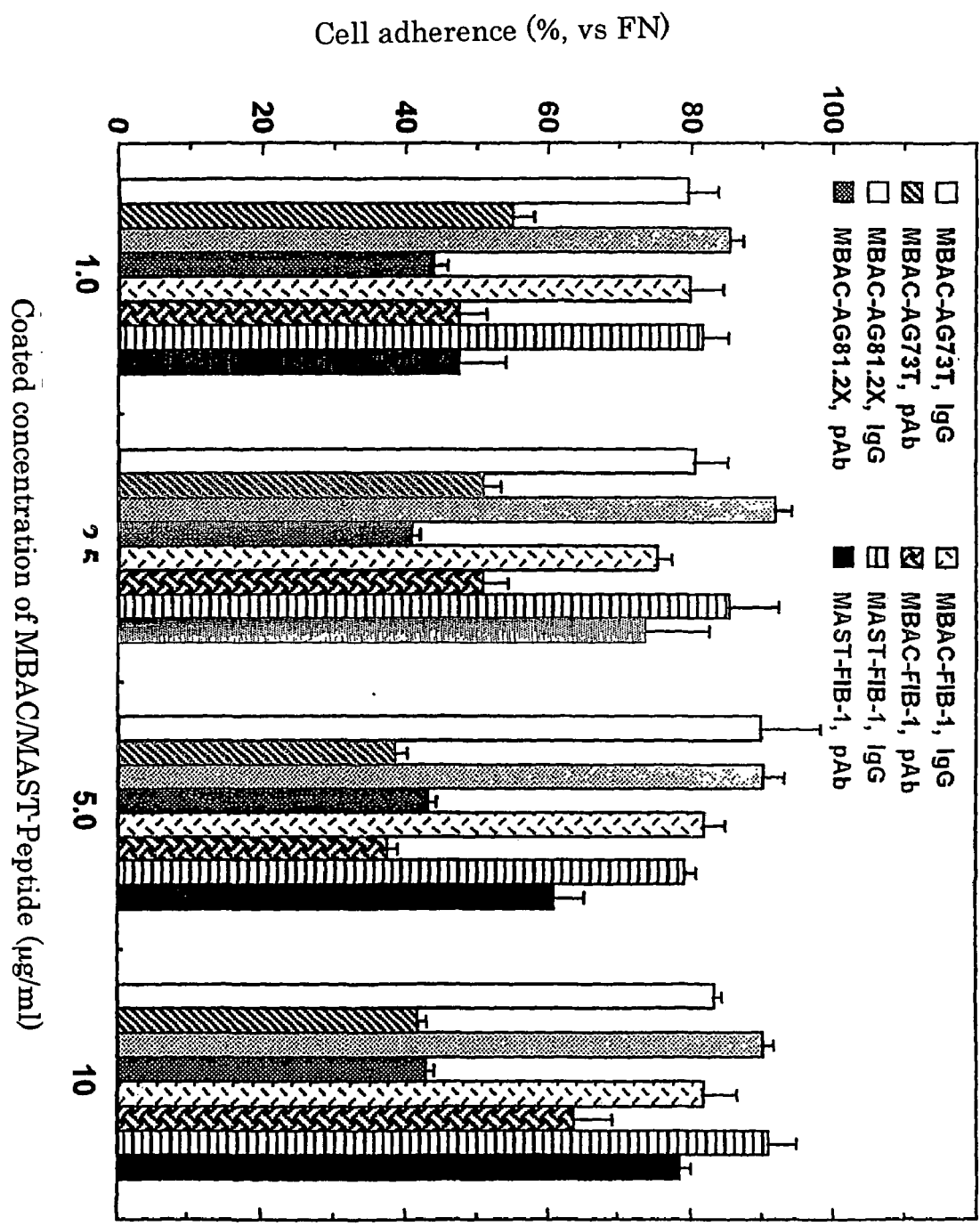
FIG. 12 is a graph showing that the adhesion of T2 cells was specifically inhibited when pseudomatrix MBAC-peptides, diluted to the concentration of 1-10 μg/ml in the serum-free medium and adsorbed/immobilized on wells, were treated with polyclonal antibodies for the peptides.

Inhibition of Adhesion of T2 Cells to the Immobilized Pseudomatrix by the Treatment with Polyclonal Antibodies for the Peptides Each pseudomatrix prepared in Example 13 to which cell adhesion peptide was bound (MBAC-peptide) was diluted in DMEM medium to the concentration of 1-10 μg/ml, poured into a 96-well by 100 μl each, and left still overnight in a $CO_2$ incubator to be adsorbed and immobilized on the wells. Non-adsorbed MBAC-peptides were removed by rinsing well with DMEM medium. Next, 100 μl of antibodies diluted with serum-free DMEM to the concentration of 4-10 μg/ml was poured into a well, incubated for 2-4 hours to let the antibodies bind to the peptides. Normal IgG was used for control groups. Antibodies were removed after the treatment, T2 cells suspended at the concentration of $6\times10^5$ cells/ml were seeded by 100 μl each. After 1-day serum-free culture, T2 cells were fixed with 100 μl of methanol for 5 minutes, and stained with 50 μl of 0.4% crystal violet for 30 minutes. Excessive staining was washed with water, and the number of adhering cells was counted based on the absorbance of cytoplasm (A595). The results are shown in FIG. 12.

In all measurements, MBAC-AG73T, -AG81.2X, -FIB-1 exhibited the same level of cell adhesion ability as in the case where FN was coated. Moreover, because the cell adhesion was specifically inhibited by the treatment with the antibodies for peptides, T2 cells are considered to adhere through the peptides.

The similar results are obtained for MAST-peptide prepared with MAST instead of MBAC. As an example, the result obtained for MAST-FIB-1 is shown in FIG. 12. The reason why the degree of inhibition by the antibody is low when MAST-FIB-1 is immobilized at the concentration of 2.5-10 μg/ml is that the affinity to the cells is far stronger than MBAC-FIB-1 as in Example 15. When the concentration is adjusted to 1 μg/ml, immobilized MBAC-FIB-1 and MAST-FIB-1 were equally inhibited by the treatment of anti-FIB-1 antibody.

Example 17

Inhibition of T2 Cells' Adhesion to the Immobilized Pseudomatrices by Heparin Treatment Pseudomatrices prepared in Example 13 to which each cell adhesion peptide was bound (MBAC-peptide) was diluted in DMEM medium to the concentration of 1-10 μg/ml, poured into 96-wells by 100 μl each, and left still overnight in a $CO_2$ incubator to be adsorbed and immobilized on the wells. Non-adsorbed MBAC-peptide was removed by rinsing well with DMEM medium. Next, 100 μl of DMEM in which 1 mg/ml of heparin was dissolved was poured into the wells, incubated for 2 hours to allow heparin to bind to the peptides. Control groups were treated with DMEM only. Heparin was removed after the treatment, and T2 cells suspended at the concentration of $6\times10^5$ cells/ml were seeded by 100 μl each. After 1-day serum-free culture, T2 cells were fixed with 100 μl of methanol for 5 minutes, and stained with 50 μl of 0.4% crystal violet for 30 minutes. Excessive staining was washed with water, and the number of adhering cells was counted based on the absorbance of cytoplasm (A595). The results are shown in FIGS. 13 and 14.

Figure 13:
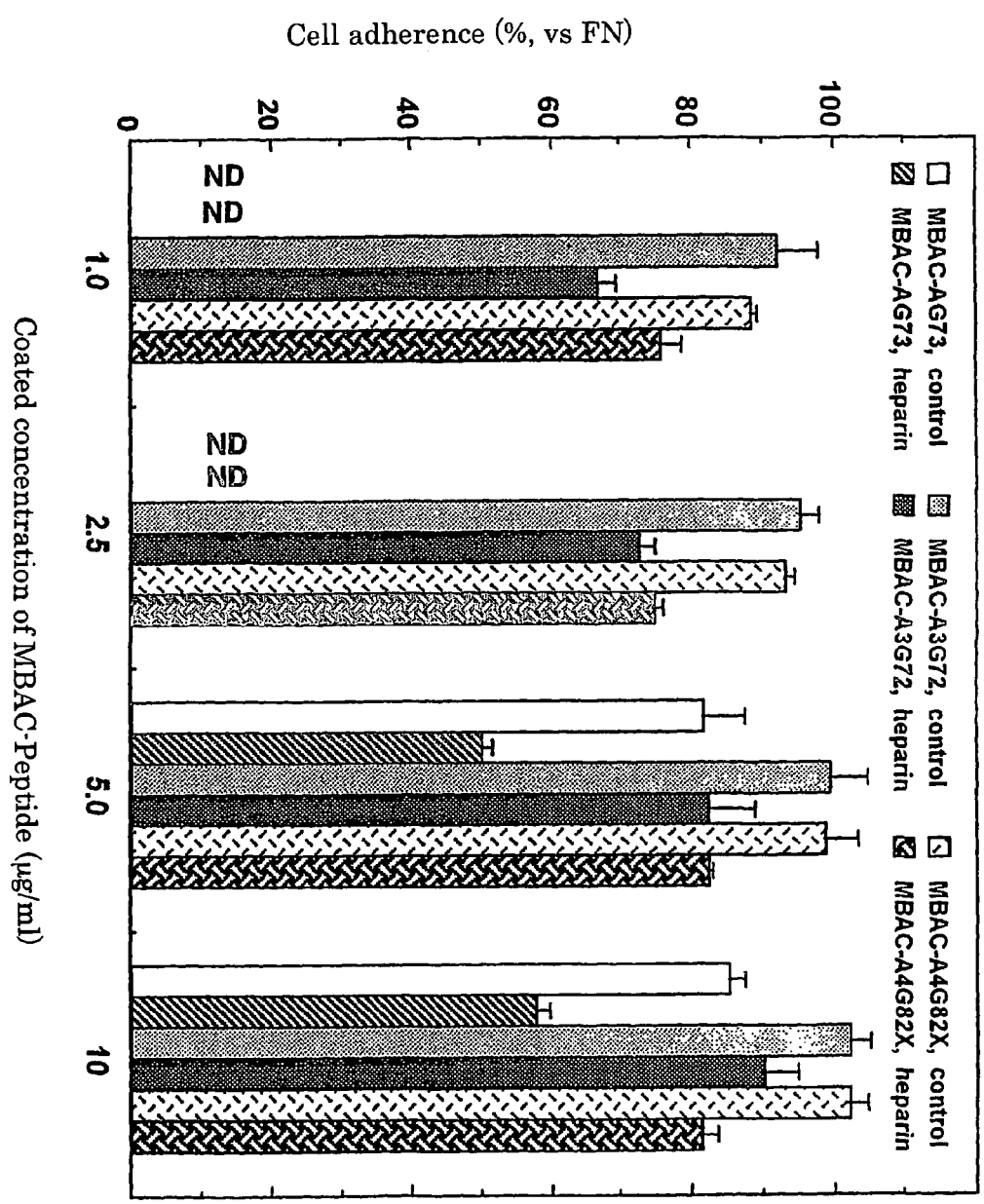
FIG. 13 is a graph showing that the adhesion of T2 cells was specifically inhibited when pseudomatrix MBAC-peptides, diluted to the concentration of 1-10 μg/ml in the serum-free medium and adsorbed/immobilized on wells, were treated with heparin.
Figure 14:
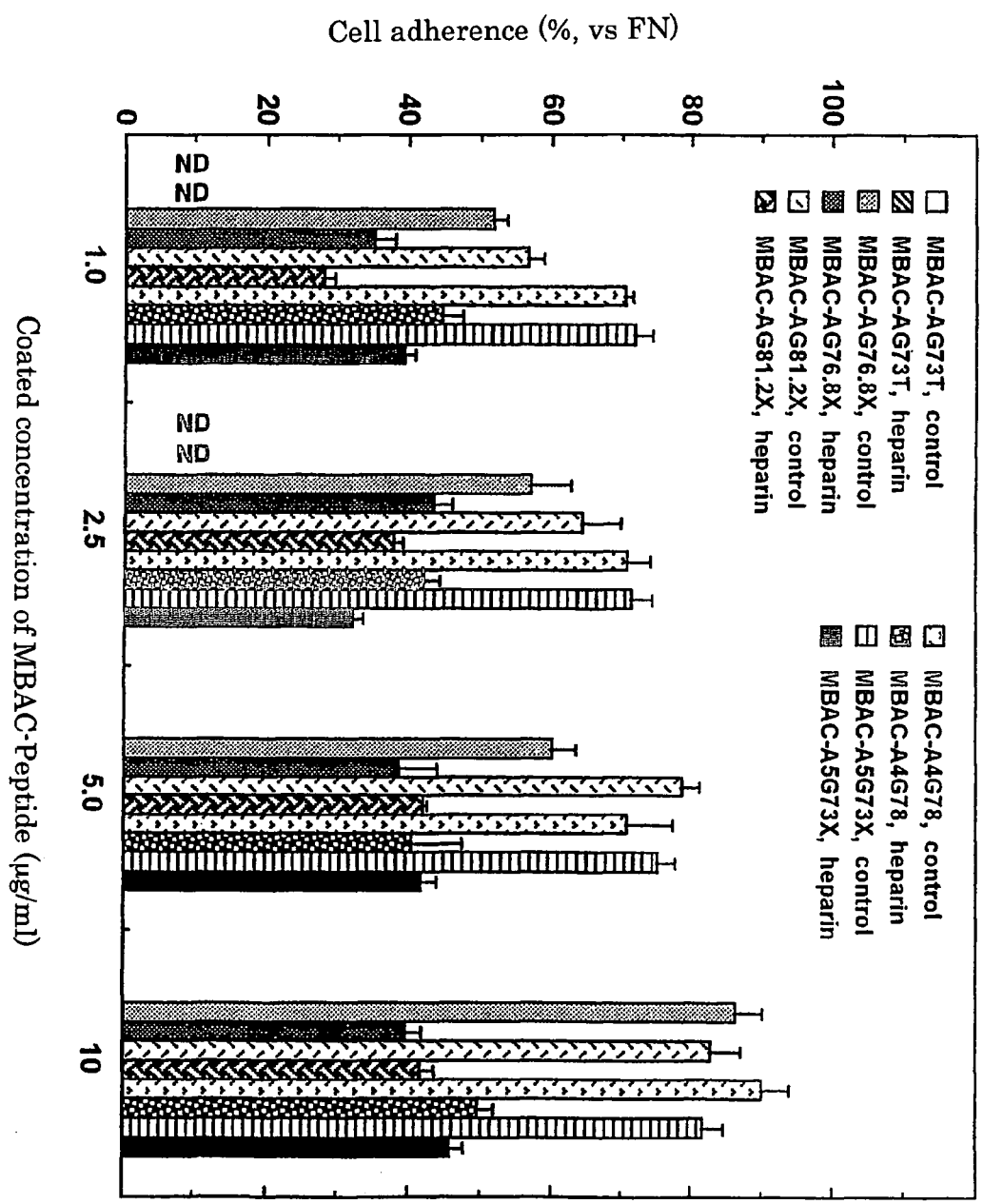
FIG. 14 is a graph showing that the adhesion of T2 cells was specifically inhibited when pseudomatrix MBAC-peptides, diluted to the concentration of 1-10 μg/ml in the serum-free medium and adsorbed/immobilized on wells were treated with heparin.

By the heparin treatment to cell adhesion peptides, the cell adhesion was specifically inhibited by 25-40% in FIG. 13 and by 35-55% in FIG. 14 in comparison to control groups. Based on this result, it is considered that T2 cells adhere to the immobilized peptides, AG73, A3G72, A4G82X in FIG. 13, and AG73T, AG76.8X, AG81.2X, A4G78, A5G73X in FIG. 14, with syndecan, an adhesion receptor having a sugar chain like heparin which is present on cell surface. The reason why the degree of inhibition by heparin in FIG. 13 is lower than that in FIG. 14 is that the affinity between the cells and the immobilized cell adhesion peptides is higher in the cases of AG73, A3G72, A4G82X (see Example 12, FIG. 9 and Table 1). In addition, with regard to some of MBAC-peptides in FIG. 14, the amount of cell adhesion decreased when they (the MBAC-peptides) were coated at the concentration of 1-2.5 µg/ml, so that the degree of inhibition by heparin decreased as well. It is presumed that this is due to the increase in the proportion of nonspecific adhesion at the cell adhesion, which was caused by the decrease in the immobilized amounts of MBAC-peptides.

In the synthesis of pseudomatrices polymer-A4G82X (FIG. 13), -AG76.8X, -AG81.2X, -A5G73X (FIG. 14), Nle that does not exist in natural proteins is used instead of Met. However, Nle exhibited the same level of cell adhesion ability as in the cases where A4G82, AG76.8, AG81.2, A5G83 were immobilized, respectively (see Example 8, FIGS. 4 and 5). Moreover, because the cell adhesion was inhibited by heparin in the same manner (see Example 10 and FIG. 7), T2 cells are considered to recognize Met and Nle with no distinction. Met often loses its bioactivity when it becomes sulfoxide or sulfone because of the oxidization of S atoms in its side chain. Though it was concerned that these pseudomatrices might be inactive, the fact that the peptides wherein Met had been replaced by Nle exhibited the same function as that of original peptides is valuable for securing the higher stability of pseudomatrices and broadening the use thereof.

Example 18

Application of Pseudomatrices Dissolved in Aqueous Solution Containing Ethanol, and Adhesion of T2 Cells to the Coated Pseudomatrices)

Figure 15:
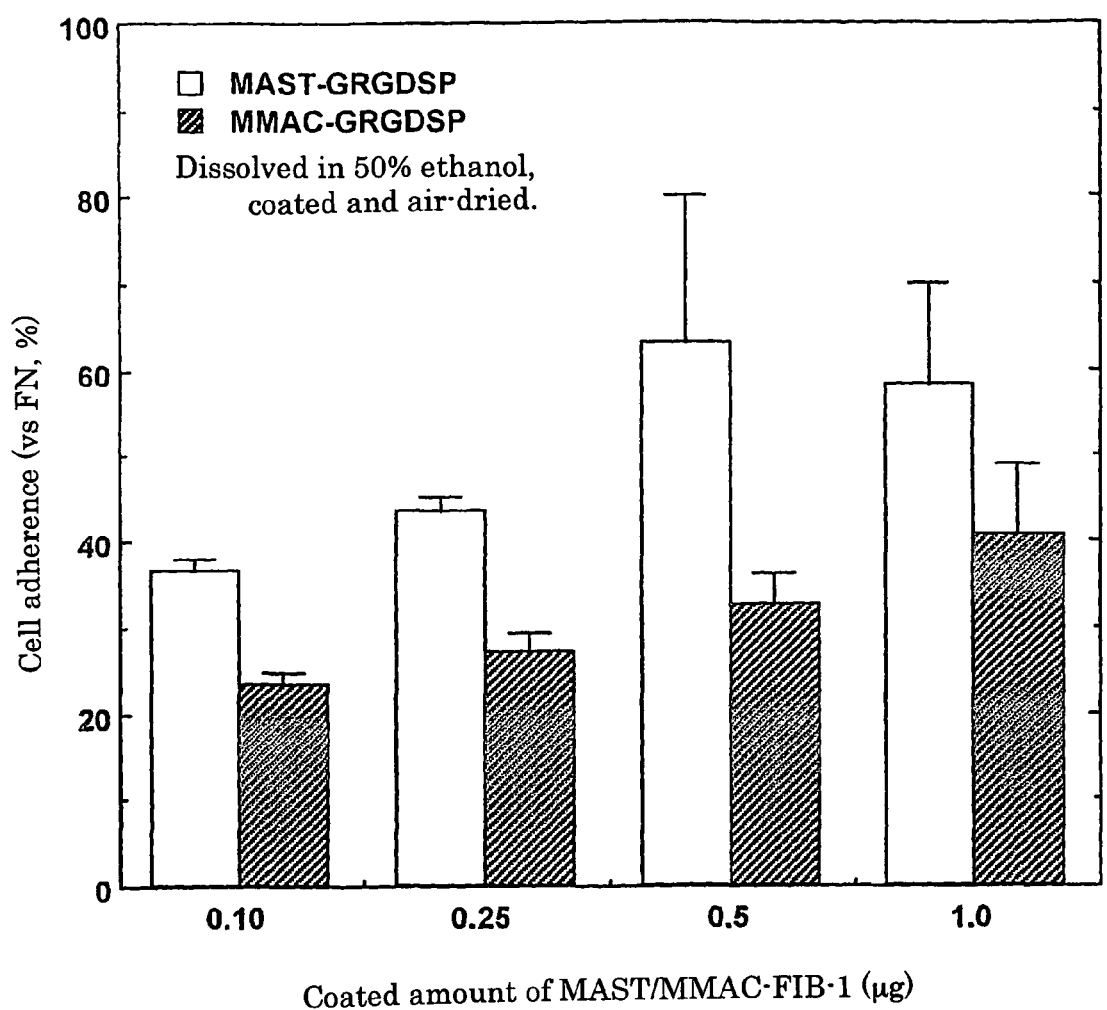
FIG. 15 is a graph showing that the adhesion level of T2 cells suspended in the serum-free medium changed in a manner depending on the coated amounts of pseudomatrices MAST-GRGDSP (SEQ ID NO: 22) and MMAC-GRGDSP (SEQ ID NO: 22) (0.1-1.0 μg/well) that were diluted to the concentration of 2-20 μg/ml with 50% ethanol, poured into wells by 50 μl each, and air-dried/immobilized, by adopting a case where FN was coated, as a standard.

50 µl of 2-20 µg/ml MAST-GRGDSP (Gly-Arg-Gly-Asp-Ser-Pro) (SEQ ID NO: 22) and MMAC-GRGDSP (SEQ ID NO: 22) dissolved in 50% ethanol were poured into wells, and air-dried/immobilized. Next, the wells to which MAST-GRGDSP (SEQ ID NO: 22) and MMAC-GRGDSP (SEQ ID NO: 22) (0.1-1.0 µg/well) were coated were rinsed with the serum-free DMEM medium. T2 cells suspended in the medium at the concentration of $6 \times 10^4$ cells/100 µl were seeded, and cultured in a $CO_2$ incubator at 37° C. for 24 hours. Then, the cells were fixed with methanol, stained, and measured its absorbance according to the method in Example 7. The results are shown in FIG. 15. A culture wherein FN was coated as a standard material was conducted simultaneously. The cell adhesion on FN was shown as a standard (100%).

Ordinary proteins are denatured and inactivated under the condition of 50% ethanol. However, as is shown in Examples 21 and 22, pseudomatrices, not only MAST/MMAC-GRGDSP (SEQ ID NO: 22), exhibited the stable cell adhesion ability even when it was dissolved in 50% ethanol (see Examples 21, 22, and FIGS. 18, 19). This performance was not lost even after the coated wells were left for a long time at room temperature.

The adhesion of T2 cells to both pseudomatrices is slightly lower than that of the standard cell adhesion protein FN. In a case of GRGDSP (SEQ ID NO: 22) peptide, there is only one amino acid residue, —CO.NH-Gly- that can serve as a spacer that secures a distance to a hydrophobic binding-adsorptive polymer and reduce steric hindrance. However, in a case of FIB-1 peptide having the five amino acid residues, —CO.NH-Tyr-Ala-Val-Thr-Gly- (SEQ ID NO: 23) that can serve as a spacer and containing GRGDSP (SEQ ID NO: 22) sequence, the same level of cell adhesion ability as that of FN was exhibited (see Examples 21, 22, and FIGS. 18, 19). Therefore, it is considered that at least one of the reasons why the mount of T2 cell adhesion is slightly low in the case of MAST/MMAC-GRGDSP (SEQ ID NO: 22) can be attributable to a steric hindrance to GRGDSP (SEQ ID NO: 22) peptide by hydrophobic binding-adsorptive polymers. The GRGDSP (SEQ ID NO: 22) peptide bound to MAST hydrophobic binding-adsorptive polymer exhibits the larger amount of cell adhesion than that of the same peptide bound to MMAC polymer, because MAST-GRGDSP (SEQ ID NO: 22) exhibits a higher adsorption to polystyrene wells.

Example 19

Figure 16:
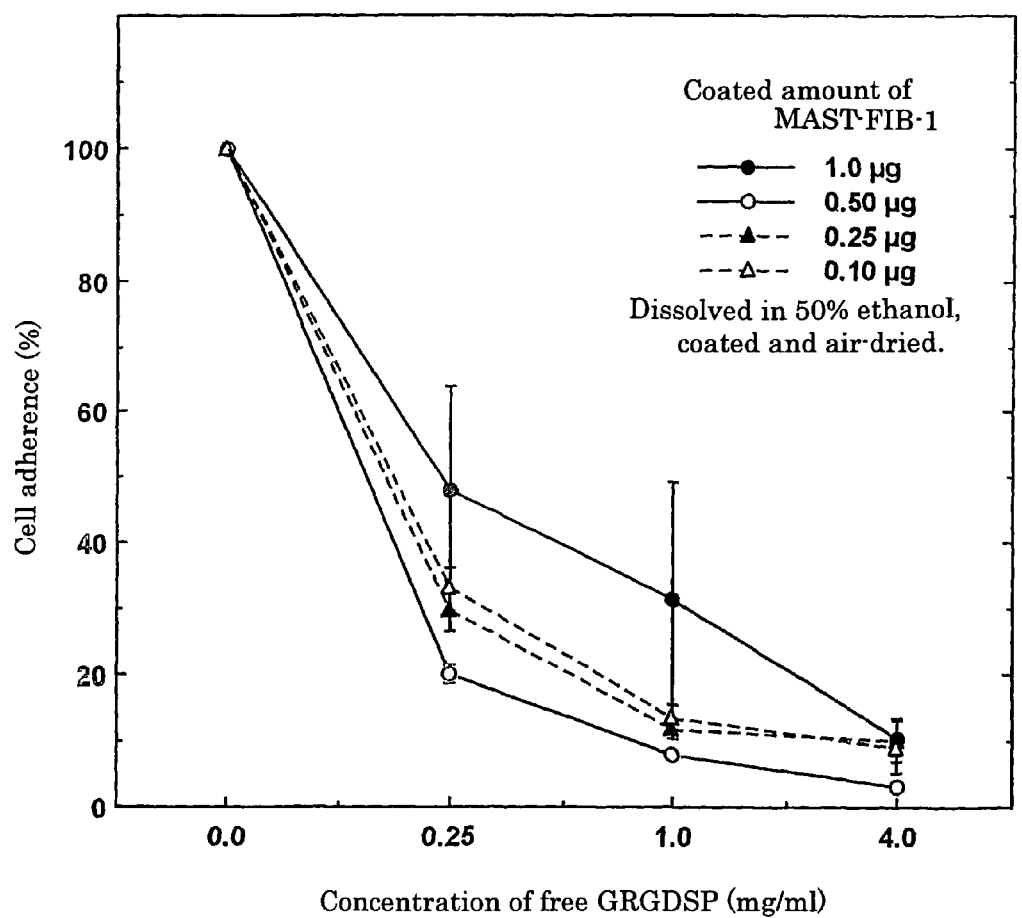
FIG. 16 is a graph showing that the adhesion of T2 cells to pseudomatrix MAST-GRGDSP (SEQ ID NO: 22) (0.1-1.0 μg/well) which was diluted with 50% ethanol, poured into wells, and air-dried/immobilized, was competitively inhibited by the free GRGDSP (SEQ ID NO: 22) peptide.

Adhesion of T2 Cells to Wells Wherein MAST-GRGDSP (SEQ ID NO: 22) Pseudomatrix Dissolved in Aqueous Solution Containing Ethanol and Air-Dried/Immobilized, and Concentration Dependency of Competitive Inhibition by Free GRGDSP (SEQ ID NO: 22) Peptide In the same manner as in Example 18, MAST-GRGDSP (SEQ ID NO: 22) was dissolved in 50% ethanol, air-dried/immobilized on wells, and T2 cells were seeded/cultured thereon. Separately, just before the cells were seeded, 0.25-4.0 mg/ml of free GRGDSP (SEQ ID NO: 22) peptide was added to the cell suspension, and the culture and the subsequent measurement of absorbance were conducted in the same manner as described above. The results are shown in FIG. 16. With the increase in the concentration of free GRGDSP (SEQ ID NO: 22) peptide, the cell adhesion was gradually inhibited and almost completely inhibited at 4.0 mg/ml. This suggests that T2 cells specifically bind/adhere through immobilized GRGDSP (SEQ ID NO: 22). Further, when the applied amount of MAST-GRGDSP (SEQ ID NO: 22) was decreased, the immobilized amount of GRGDSP (SEQ ID NO: 22) decreased, and the competitive inhibition by free GRGDSP (SEQ ID NO: 22) peptide worked more effectively.

Example 20

Figure 17:
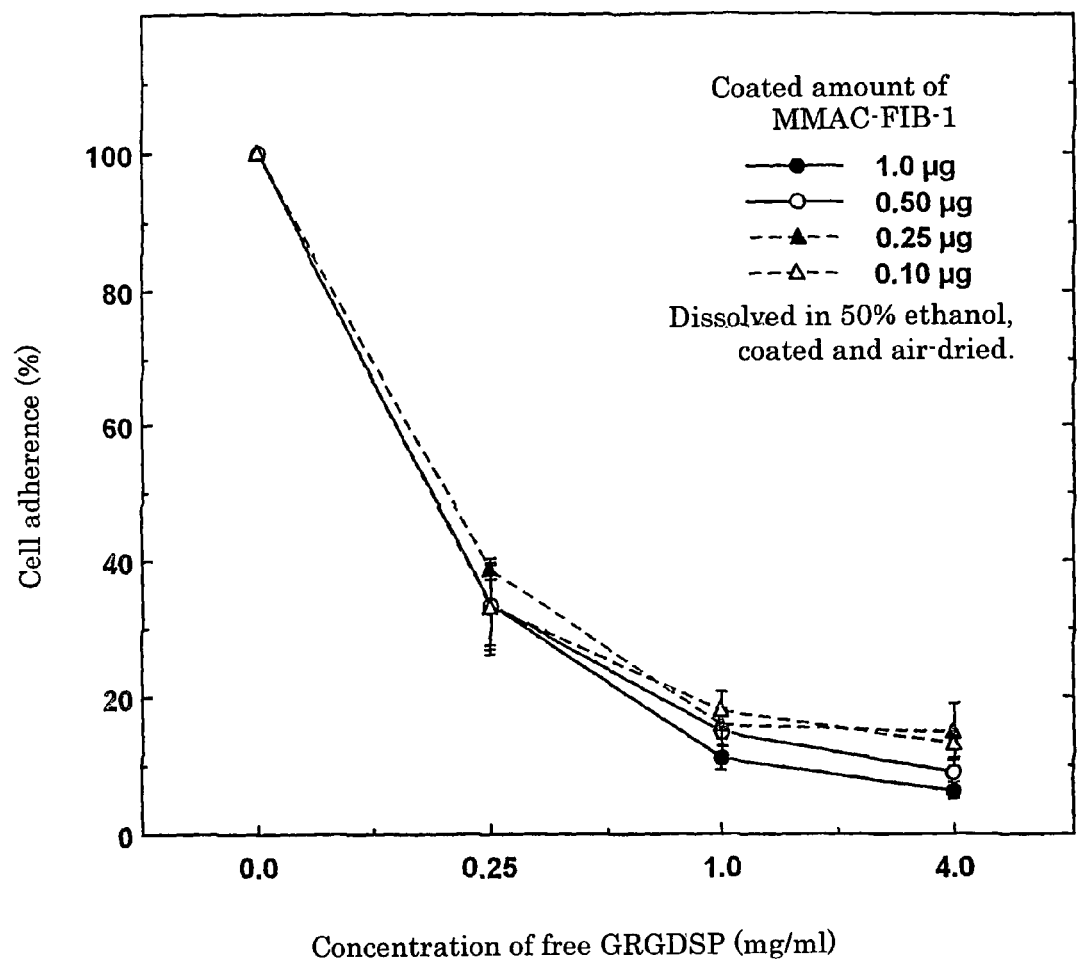
FIG. 17 is a graph showing that the adhesion of T2 cells to pseudomatrix MMAC-GRGDSP (SEQ ID NO: 22) (0.1-1.0 μg/well) which was diluted with 50% ethanol, poured into wells, and air-dried/immobilized, was competitively inhibited by the free GRGDSP (SEQ ID NO: 22) peptide.

Adhesion of T2 Cells to Wells Wherein MMAC-GRGDSP (SEQ ID NO: 22) Pseudomatrix Dissolved in Aqueous Solution Containing Ethanol and Air-Dried/Immobilized, and Concentration Dependency of Competitive Inhibition by Free GRGDSP (SEQ ID NO: 22) Peptide In the same manner as in Example 18, MMAC-GRGDSP (SEQ ID NO: 22) was dissolved in 50% ethanol, air-dried/immobilized on wells, and T2 cells were seeded/cultured thereon. Separately, just before the cells were seeded, 0.25-4.0 mg/ml of free GRGDSP (SEQ ID NO: 22) peptide was added to the cell suspension, and the culture and the subsequent measurement of absorbance were conducted in the same manner as described above. The results are shown in FIG. 17. As with the case with Example 19, with the increase in the concentration of free GRGDSP (SEQ ID NO: 22) peptide, the cell adhesion was gradually inhibited, and almost completely inhibited at 1.0-4.0 mg/ml. This suggests that T2 cells specifically bind/adhere through immobilized GRGDSP (SEQ ID NO: 22) as in Example 19.

Example 21

Figure 18:
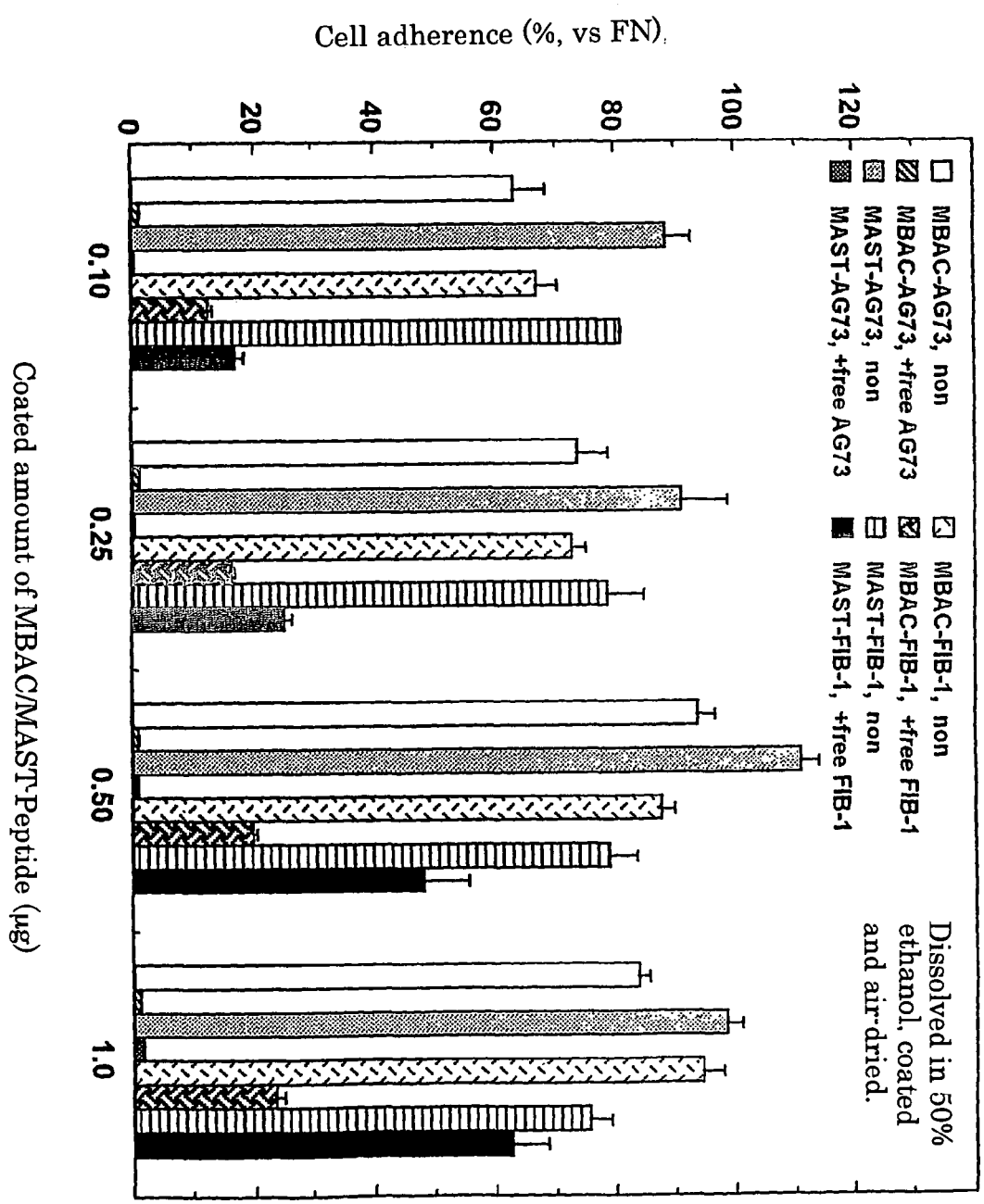
FIG. 18 is a graph showing that the adhesion of T2 cells to pseudomatrices MBAC-peptides and MAST-peptides (0.1-1.0 μg/well) which were diluted with 50% ethanol, poured into wells, and air-dried/immobilized, was competitively inhibited by the free peptides.

Adhesion of T2 Cells to Wells Wherein Pseudomatrices Dissolved in Aqueous Solution Containing Ethanol and Air-Dried/Immobilized, and Competitive Inhibition by the Free Peptide In the same manner as in Example 18, MBAC/MAST-AG73 and -FIB-1 were dissolved in 50% ethanol, air-dried/ immobilized on wells, and T2 cells were seeded/cultured thereon. Separately, just before the cells were seeded, 0.25 mg/ml of free AG73 or FIB-1 peptide was added to the cell suspension, and the culture and the subsequent measurement of absorbance were conducted in the same manner as described above. The results are shown in FIG. 18. T2 cells adhered to the immobilized AG73 and FIB-1 peptides similarly to the case where FN was coated. Moreover, the cell adhesion was almost completely inhibited by free AG73 peptide. In case of the immobilized FIB-1 peptide, in particular, MAST-FIB-1, the competitive inhibition caused by free FIB peptide worked more effectively in accordance with the decrease in the amount of immobilized FIB-1.

Example 22

Figure 19:
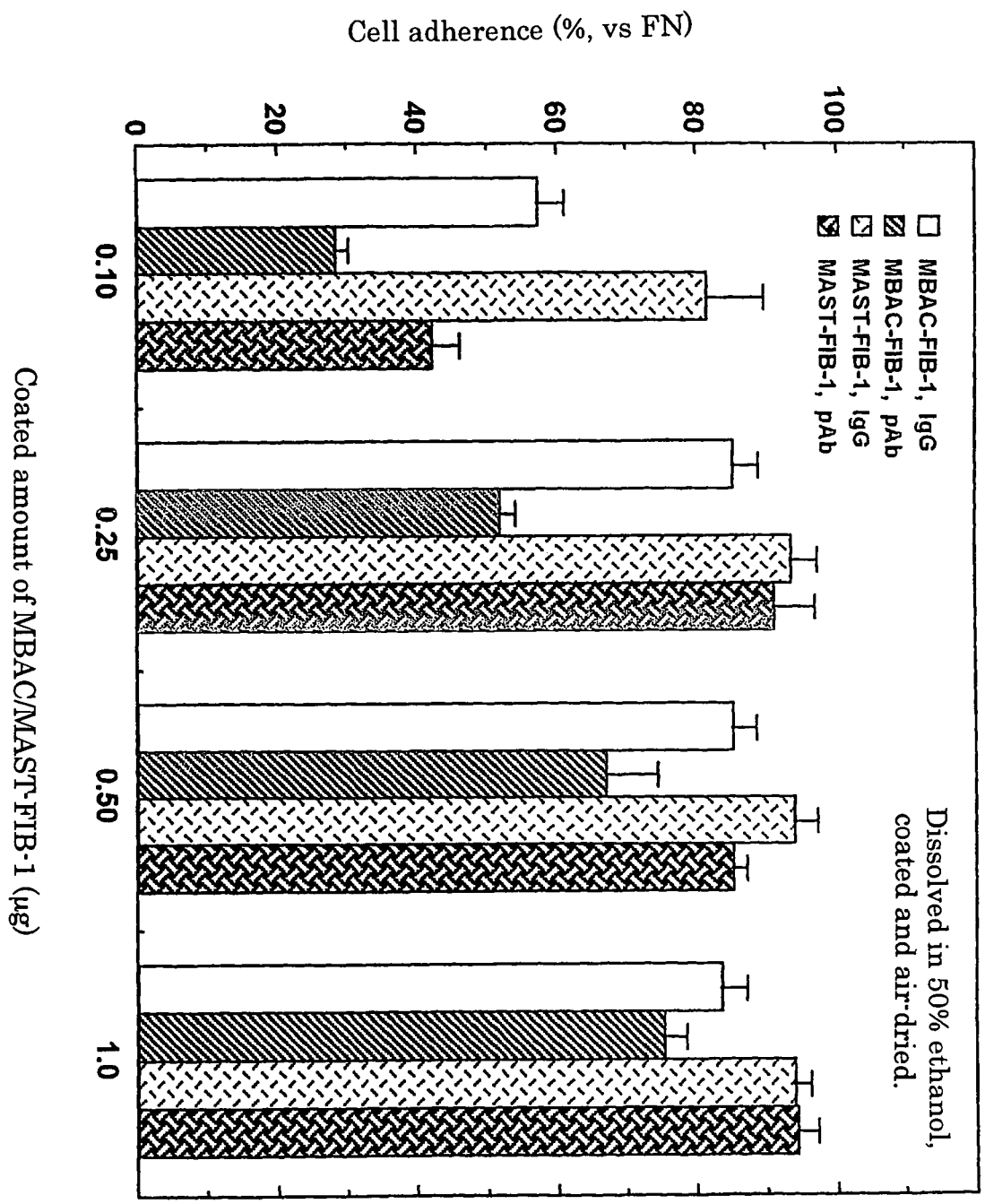
FIG. 19 is a graph showing that the adhesion of T2 cells was specifically inhibited when the pseudomatrices MBAC-FIB-1 and MAST-FIB-1 (0.1-1.0 μg/well) which were diluted with 50% ethanol, poured into wells, and air-dried/immobilized, were treated with a polyclonal antibody to FIB-1 peptide.

Inhibition of T2 Cells Adhesion by the Treatment with Anti-FIB-1 Peptide Antibody after MBAC/Mast-FIB-1 Dissolved in Aqueous Solution Containing Ethanol is Air-Dried/Immobilized In the same manner as in Example 21, MBAC/MAST-FIB-1 was diluted with 50% ethanol, poured into wells, and air-dried/immobilized. Before T2 cells were seeded, 100 μl of 4 μg/ml anti-FIB-1 polyclonal antibody was poured into the well, and incubated for 4 hours to allow the antibody to bind to the immobilized FIB-1 peptide. Controls were treated with normal IgG. T2 cells were cultured, fixed, and stained in the same manner as in Example 21. The results are shown in FIG. 19. At FIB-1 concentration of 0.1-0.25 μg/well, the cell adhesion was specifically inhibited by the antibody.

INDUSTRIAL APPLICABILITY

According to the present invention, cells can proliferate in a good condition during cell culture without detaching, even if an excessive loading heavier than a usual one is put with a stretching cell culture apparatus, by the use of silicone wells that are coated with a hydrophobic binding-adsorptive polymer.

In addition, according to the present invention, the immobilized preparation of cell adhesion proteins or peptides of the present invention is more stable than the preparation in which the cell adhesion proteins are directly immobilized. The immobilized preparation of peptides is also an extremely useful substitution for cell adhesion proteins, because cell adhesion peptides are not expensive. Further, the performance of cell adhesion peptide shows a sufficient activity in comparison with FN, a representative adhesion protein. Still further, immobilized LN α-chain G-domain peptides, which are stable in structure and inexpensive, are extremely effective as substitutes for LN. In addition, pseudomatrices can be chemically synthesized perfectly. In cases where culture substrates are derived from organism, it is difficult to eliminate a risk of contamination with prion, virus, bacteria, etc. during production processes. However, as long as completely synthesized products are used, this risk can be eliminated upon producing artificial tissues or artificial organs, therefore, it is highly advantageous in production.

---

The invention claimed is:

1. An immobilized preparation of a cell adhesion protein or peptide for cell culture, comprising:
   a hydrophobic cell culture substrate,
   a cell adhesion protein or peptide,
   a hydrophobic binding-adsorptive polymer to which the cell adhesion protein or peptide has been covalently bound,
   wherein the hydrophobic binding-adsorptive polymer to which the cell adhesion protein or peptide is covalently bound, is adsorbed to the hydrophobic cell culture substrate by hydrophobic binding and not by chemical bonding, and
   wherein the hydrophobic binding-adsorptive polymer is selected from a copolymer of maleic anhydride and styrene; a copolymer of maleic anhydride and butyl vinyl ether; and a copolymer of maleic anhydride and hexyl vinyl ether.

2. A method for producing an immobilized preparation of a cell adhesion protein or peptide for cell culture, comprising:
   (a) reacting a functional group of a hydrophobic binding-adsorptive polymer with a cell adhesion protein or peptide, the functional group being capable of reacting with the cell adhesion protein or peptide to produce a hydrophobic binding-adsorptive polymer covalently bound to the cell adhesion protein or peptide, and
   (b) coating a hydrophobic cell culture substrate with the hydrophobic binding-adsorptive polymer covalently bound to the cell adhesion protein or peptide from step (a), so that the hydrophobic binding-adsorptive polymer covalently bound to the cell adhesion protein or peptide adsorbs to the hydrophobic cell culture substrate by hydrophobic binding and not by chemical bonding,
   wherein the hydrophobic binding-adsorptive polymer is selected from a copolymer of maleic anhydride and styrene; a copolymer of maleic anhydride and butyl vinyl ether; and a copolymer of maleic anhydride and hexyl vinyl ether.

3. A method for producing an immobilized preparation of a cell adhesion protein or peptide for cell culture, comprising:
   (a) coating a hydrophobic cell culture substrate with a hydrophobic binding-adsorptive polymer, so that hydrophobic binding-adsorptive polymer adsorbs to the hydrophobic cell culture substrate by hydrophobic binding and not by chemical bonding to produce a hydrophobic cell culture substrate having the hydrophobic binding-adsorptive polymer adsorbed thereto;
   (b) reacting a functional group of the hydrophobic binding-adsorptive polymer bound to the hydrophobic cell culture substrate from step (a) with a cell adhesion protein or peptide, the functional group being capable of reacting with the cell adhesion protein or the peptide to produce a hydrophobic cell culture substrate having a hydrophobic binding-adsorptive polymer adsorbed thereto wherein the functional group of the hydrophobic binding-adsorptive polymer bound thereto is covalently bound to the cell adhesion protein or peptide, and
   wherein the hydrophobic binding-adsorptive polymer is selected from a copolymer of maleic anhydride and styrene; a copolymer of maleic anhydride and butyl vinyl ether; and a copolymer of maleic anhydride and hexyl vinyl ether.

* * * * *